US008823382B2

(12) United States Patent
Rondoni et al.

(10) Patent No.: US 8,823,382 B2
(45) Date of Patent: Sep. 2, 2014

(54) SYSTEM AND METHOD FOR MONITORING A POWER SOURCE OF AN IMPLANTABLE MEDICAL DEVICE

(75) Inventors: John C. Rondoni, Plymouth, MN (US); Mukul Jain, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1611 days.

(21) Appl. No.: 12/112,144

(22) Filed: Apr. 30, 2008

(65) Prior Publication Data

US 2009/0273349 A1 Nov. 5, 2009

(51) Int. Cl.
*G01N 27/416* (2006.01)
*A61N 1/37* (2006.01)
*G01R 31/36* (2006.01)

(52) U.S. Cl.
CPC ............ *A61N 1/3708* (2013.01); *G01R 31/362* (2013.01); *G01R 31/3662* (2013.01)
USPC ............................ 324/430; 320/134; 320/162

(58) Field of Classification Search
USPC .......... 324/426, 430; 320/134, 136, 157, 159, 320/162, 164
See application file for complete search history.

(56) References Cited

U.S. PATENT DOCUMENTS

| 4,026,305 A | 5/1977 | Brownlee et al. |
| 4,041,955 A | 8/1977 | Kelly et al. |
| 4,071,032 A | 1/1978 | Schulman |
| 4,082,097 A | 4/1978 | Mann et al. |
| 4,124,533 A | 11/1978 | Knowles et al. |
| 4,248,237 A | 2/1981 | Kenny |
| 4,254,775 A | 3/1981 | Langer |
| 4,313,079 A | 1/1982 | Lee |
| 4,373,527 A | 2/1983 | Fischell |
| 4,390,020 A | 6/1983 | Herpers |
| 4,448,197 A | 5/1984 | Nappholz et al. |
| 4,542,532 A | 9/1985 | McQuilkin |
| 4,550,370 A | 10/1985 | Baker |
| 4,556,061 A | 12/1985 | Barreras et al. |
| 4,677,363 A | 6/1987 | Kopmann |
| 4,692,147 A | 9/1987 | Duggan |
| 4,715,381 A | 12/1987 | Moberg |
| 4,949,046 A | 8/1990 | Seyfang |
| 4,952,862 A | 8/1990 | Biagetti et al. |

(Continued)

FOREIGN PATENT DOCUMENTS

| EP | 0593198 | 4/1994 |
| WO | WO91/10471 | 7/1991 |

(Continued)

*Primary Examiner* — Edward H Tso
*Assistant Examiner* — Aaron Piggush
(74) *Attorney, Agent, or Firm* — Beth L. McMahon

(57) ABSTRACT

Techniques for monitoring a battery of an implantable medical device are disclosed. First and second current sources are provided to draw currents having amplitudes of $I_1$ and $I_2$, respectively, from the battery. First and second voltage measurements, $V_1$ and $V_2$, are obtained when first and second combinations, respectively, of the first and second current sources are selectively activated. Battery impedance is determined using the current amplitudes $I_1$ and $I_2$ and the voltage measurements $V_1$ and $V_2$. The impedance measurement may be used to obtain an open-circuit voltage of the battery without the need to disconnect the battery from circuitry to which it provides power. Battery impedance and/or open-circuit battery voltage may then be used to determine an estimated time until an action is required involving the battery, which may include activation of an ERI or EOL indicator, or initiation of a recharge session.

40 Claims, 13 Drawing Sheets

(56) References Cited

U.S. PATENT DOCUMENTS

| | | |
|---|---|---|
| 5,080,096 A | 1/1992 | Hooper |
| 5,107,833 A | 4/1992 | Barsness |
| 5,117,825 A | 6/1992 | Grevious |
| 5,127,404 A | 7/1992 | Wyborny et al. |
| 5,137,020 A * | 8/1992 | Wayne et al. .................. 607/29 |
| 5,168,871 A | 12/1992 | Grevious |
| 5,185,566 A | 2/1993 | Goedken et al. |
| 5,292,343 A | 3/1994 | Blanchette et al. |
| 5,314,450 A | 5/1994 | Thompson |
| 5,324,315 A | 6/1994 | Grevious |
| 5,344,431 A | 9/1994 | Merritt et al. |
| 5,349,540 A | 9/1994 | Birkle et al. |
| 5,350,411 A | 9/1994 | Ryan et al. |
| 5,354,319 A | 10/1994 | Wyborny et al. |
| 5,369,364 A * | 11/1994 | Renirie et al. ................. 324/430 |
| 5,370,668 A | 12/1994 | Shelton et al. |
| 5,383,909 A | 1/1995 | Keimel |
| 5,391,193 A | 2/1995 | Thompson |
| 5,402,070 A | 3/1995 | Shelton et al. |
| 5,402,794 A | 4/1995 | Wahlstrand et al. |
| 5,458,624 A | 10/1995 | Renirie et al. |
| 5,591,217 A | 1/1997 | Barreras |
| 5,620,474 A | 4/1997 | Koopman |
| 5,693,076 A | 12/1997 | Kaemmerer |
| 5,723,971 A | 3/1998 | Sakai et al. |
| 5,741,307 A | 4/1998 | Kroll |
| 5,741,313 A | 4/1998 | Davis et al. |
| 5,744,931 A | 4/1998 | Arai et al. |
| 5,752,976 A | 5/1998 | Duffin et al. |
| 5,764,034 A | 6/1998 | Bowman et al. |
| 5,766,232 A | 6/1998 | Grevious et al. |
| 5,769,873 A | 6/1998 | Zadeh |
| 5,769,877 A | 6/1998 | Barreras, Sr. |
| 5,789,900 A | 8/1998 | Hasegawa et al. |
| 5,800,472 A | 9/1998 | Mann |
| 5,807,397 A | 9/1998 | Barreras |
| 5,861,019 A | 1/1999 | Sun et al. |
| 5,904,708 A | 5/1999 | Goedeke |
| 5,925,068 A | 7/1999 | Kroll |
| 5,994,876 A | 11/1999 | Canny et al. |
| 6,016,448 A | 1/2000 | Busacker et al. |
| 6,099,495 A | 8/2000 | Kinghorn et al. |
| 6,108,579 A | 8/2000 | Snell et al. |
| 6,148,235 A | 11/2000 | Kuiper |
| 6,154,675 A | 11/2000 | Juran et al. |
| 6,166,518 A | 12/2000 | Echarri et al. |
| 6,167,309 A | 12/2000 | Lyden |
| 6,169,387 B1 | 1/2001 | Kaib |
| 6,185,461 B1 | 2/2001 | Er |
| 6,198,253 B1 | 3/2001 | Kurle et al. |
| 6,198,968 B1 | 3/2001 | Prutchi et al. |
| 6,272,379 B1 | 8/2001 | Fischell et al. |
| 6,329,793 B1 | 12/2001 | Bertness et al. |
| 6,359,441 B1 | 3/2002 | Bertness |
| 6,400,988 B1 | 6/2002 | Gurewitsch |
| 6,490,484 B2 | 12/2002 | Dooley et al. |
| 6,516,227 B1 | 2/2003 | Meadows et al. |
| 6,584,355 B2 | 6/2003 | Stessman |
| 6,671,552 B2 | 12/2003 | Merritt et al. |
| 6,842,460 B1 | 1/2005 | Olkkonen et al. |
| 6,870,349 B2 | 3/2005 | Cook |
| 6,901,293 B2 | 5/2005 | Rogers et al. |
| 6,928,372 B2 | 8/2005 | Pozsgay et al. |
| 7,001,359 B2 | 2/2006 | Rogers |
| 7,142,923 B2 | 11/2006 | North |
| 7,245,107 B2 * | 7/2007 | Moore et al. .................. 320/112 |
| 7,317,947 B2 | 1/2008 | Wahlstrand et al. |
| 7,542,801 B2 | 6/2009 | Rogers et al. |
| 2005/0277994 A1 | 12/2005 | McNamee et al. |
| 2006/0025828 A1 | 2/2006 | Armstrong et al. |
| 2007/0063683 A1 | 3/2007 | Coq et al. |

FOREIGN PATENT DOCUMENTS

| | | |
|---|---|---|
| WO | WO01/05466 | 1/1994 |
| WO | WO96/20754 | 7/1996 |
| WO | WO00/24459 | 5/2000 |
| WO | WO01/08749 | 2/2001 |
| WO | WO02/074368 | 9/2002 |

* cited by examiner

SYSTEM AND METHOD FOR MONITORING A POWER SOURCE OF AN IMPLANTABLE MEDICAL DEVICE

BACKGROUND

The medical device industry produces a wide variety of electronic devices for treating patient medical conditions. Depending upon the medical condition, medical devices can be surgically implanted or connected externally to the patient receiving treatment. For example, implantable neurostimulators are available for the treatment of pain, movement disorders such as Parkinson's disease, essential tremor, dystonia, gastric disorders, incontinence, sexual disfunction, migraine headaches, and other conditions. Other examples of IMDs include, but are not limited to, implantable drug infusion pumps, cardioverters, cardiac pacemakers, defibrillators, and cochlear implants.

Because IMDs provide important, oftentimes life-sustaining, medical care to patients from the power supplied by a single component power source, usually a battery, the ability to know the status of that power source is critical. When a power source's charge has nearly run down, the power source must either be replaced or recharged. The failure to do so could result in the untimely failure of the IMD's ability to deliver therapy to the patient.

Since it is often critical for patients' well-being that IMDs do not cease operating, it is common for IMDs to monitor the level of battery depletion and to provide some indication when the depletion reaches a level at which the battery should be replaced. In the case of IMDs employing a non-rechargeable battery, it is typical for the IMD to monitor battery energy and depletion and develop an "Elective Replacement Indicator" (ERI). This ERI indicates when the battery depletion reaches a level such that replacement will soon be needed.

Once the ERI indicator has been activated, circuitry in the IMD may respond by switching or deactivating operating modes to lower power consumption. This will prolong the interval between ERI and the time when the battery is completely depleted, a condition referred to as battery End-of-Life (EOL). For example, internal diagnostic functions and advanced rate-response functions may be discontinued upon issuance of ERI. Additionally, in the case of IMDs that are delivering electrical stimulation pulses, frequency or amplitude of the delivered pulses may be decreased to conserve energy. This will allow the IMD to continue to operate for at least some minimum amount of time after issuance of an ERI. In this way, the physician will have sufficient time to take appropriate action. For an IMD employing a non-rechargeable power source, this will involve replacing the device before battery EOL.

While it is important to indicate ERI soon enough to allow for replacement of the device, it is also important not to trigger ERI too early or due to transient faults. If ERI is indicated too early, sudden operational changes associated with ERI may be made before such modifications are actually necessary. Thus, it is desirable to have an accurate estimate of the battery capacity that has been used and/or the battery capacity that remains to be used so that ERI is as accurate as possible.

In devices that employ a rechargeable power source, there is no need to replace the device when the battery is depleted. Instead, the power source is merely recharged via transcutaneous transmission of energy. In this case, an external power supply is operatively coupled with the rechargeable power source of the implantable medical device, often through an inductive link. Charging current is delivered to the rechargeable power source until the rechargeable power source is replenished. The implantable medical device may then continue to deliver therapy to the patient until the rechargeable power source has again been depleted and the process is repeated.

Even in the case of a rechargeable power source, obtaining an accurate determination of the amount of charge remaining on the battery is desirable. This will allow the patient to more conveniently re-schedule the recharge session so that it may occur before battery charge has been depleted.

One mechanism for estimating the battery capacity that has been used involves measuring either open-circuit battery voltage or battery impedance. In either case, the battery must be temporarily disconnected from the circuit to which the battery supplies power. After obtaining the open-circuit voltage or impedance measurement is this manner, the measurement is compared to battery voltage depletion or impedance characteristics, respectively. This comparison provides an estimate of the battery capacity that has been used, as well as the charge remaining on the battery, and hence the time remaining before battery recharge or replacement must be initiated.

As discussed above, measuring open-circuit battery voltage or impedance within an IMD using traditional methods has required the battery to be temporarily disconnected from the circuit to which the battery supplies power. When this occurs, some alternative method of supplying power to at least the portion of the circuitry that is obtained the measurement will be required. This may involve providing a capacitor or another alternative power supply. This increases the size and complexity of the circuit design in most cases. Another mechanism for monitoring battery capacity is therefore desired.

SUMMARY OF THE INVENTION

The current invention provides a system and method for monitoring a battery of an implantable medical device (IMD). In particular, the invention relates to techniques for determining an impedance of the battery without the need to disconnect the battery from circuitry to which the battery supplies power. In one embodiment, open-circuit battery voltage may likewise be obtained without disconnecting the battery from the circuitry.

According to one aspect, a system is provided that includes a current source that is associated with a current of a first predetermined amplitude, $I_1$. When this current source is activated, the current source will either source or sink a current having an amplitude of $I_1$ regardless of variations in voltage across the current source, so long as these variations are within a predetermined range of variations.

The system also includes a second current source that either sources or sinks a current of a second predetermined amplitude, $I_2$ which may be the same as, or different from, the first predetermined amplitude $I_1$. Like the first current source, the second current source will either source or sink the current having the amplitude of $I_2$ so long as variations in voltage across the second current source are within a predetermined range of variations.

The system further comprises a measurement circuit that is capable of measuring a first voltage across the battery when a first combination of the first and the second current source is activated. In one embodiment, the first combination includes only the first current source, which is activated while the second current source remains deactivated. The measurement circuit is also capable of measuring a second voltage across the battery when a second combination of the first and the second current source is activated. In one embodiment, this second combination is only the second current source, which is activated while the first current source remains deactivated. In another embodiment, the second combination is the first and the second current sources, which are both activated at the same time.

According to one method, the system discussed above is utilized to determine battery impedance as follows. The IMD enters a passive, or quiescent, state during which therapy is not being delivered to a patient and telemetry uplink and/or downlink sessions are not being performed. This state may be entered by default, as between scheduled therapy sessions. Alternatively, the state may be entered by control, as when a control circuit such as a microprocessor selectively temporarily deactivated therapy that is being provided to the patient.

After the IMD enters the passive state, circuitry of the IMD is drawing a quiescent current from the battery. The quiescent current has a relatively constant amplitude of $I_0$, which may be an unknown value.

After the IMD enters the quiescent state, a first combination of the first and second current sources is selectively activated. For purposes of this example, the first combination will include only the first current source, which is associated with (that is, either sources or sinks) a current of the first predetermined amplitude, $I_1$, as is discussed above. According to this example, when the first current source is activated, a first voltage measurement is obtained across the battery terminals, as may be accomplished using the measurement circuit. The first current source is then deactivated.

According to this example, the first voltage measurement, $V_1$, has the following relationship to the quiescent current, $I_0$, the first predetermined current amplitude, $I_1$, the impedance of the battery, $Z_{BATTERY}$, and the open-circuit battery voltage, $V_{OC}$, which is that voltage that would be measured across the battery terminals if the battery were disconnected from the circuit to which it supplies power:

$$V_1 = V_{OC} - Z_{BATTERY}(I_0 + I_1)$$

Next, a second combination of the first and second current sources is selectively activated. For purposes of this example, it will be assumed that the second combination only includes the second current source, which either sources or sinks a current of the second predetermined amplitude, $I_2$. When the second current source is activated, a second voltage measurement, $V_2$, is obtained across the battery terminals. The second current source is then deactivated. This second voltage measurement has the following relationship to the quiescent current, $I_0$, the second predetermined current amplitude, $I_2$, the impedance of the battery, $Z_{BATTERY}$, and the open-circuit battery voltage, $V_{OC}$:

$$V_2 = V_{OC} - Z_{BATTERY}(I_0 + I_2)$$

These foregoing relationships may be manipulated to obtain the battery impedance, which may be expressed as follows:

$$Z_{BATTERY} = (V_1 - V_2)/(I_2 - I_1)$$

In this manner, the battery impedance may be determined without the need to determine the amplitude of the quiescent current or the open-circuit voltage. Most importantly, the battery impedance of a battery within an IMD may be determined without the need to disconnect the battery from the circuit to which it supplies power.

In one embodiment, the measurement circuit is capable of measuring quiescent current having an amplitude of $I_0$, as well as the voltage $V_0$ that exists across the battery terminals at the time the battery is sourcing the quiescent current. This quiescent current may then be utilized along with the battery impedance to determine open-circuit battery voltage, as follows:

$$V_{OC} = V_0 + (I_0 \times Z_{BATTERY})$$

After battery impedance, and optionally open-circuit voltage, have been determined, these values may be used to reference battery characteristic data. For instance, battery characteristic data may provide a relationship between battery impedance and the battery charge capacity that has thus far been delivered by the battery and consumed by the IMD as compared to when the battery was in the full-charged state ("battery capacity"). This battery characteristic data may be developed empirically by obtaining measurements of multiple batteries of the given battery type, and then compiling statistical distributions.

Alternatively or additionally, the battery characteristic data may provide a relationship between open-circuit battery voltage, $V_{OC}$, and the battery capacity. As is the case with impedance data, this data may be developed empirically, and may reflect a statistical distribution of batteries of a given type.

After battery capacity is determined in at least one of the foregoing ways, the battery capacity may be used to reference data that correlates battery capacity to an action that is required involving the battery. Such an action may include activation of an ERI or EOL indicator in the case of a non-rechargeable battery, or the initiation of a recharge session for a rechargeable battery. The reference data may provide an estimate of the time remaining until such an action is required, for instance. Any of the obtained information may then be provided to a user. This provided information may include the action that is to be performed in relation to the battery, the time until the action is required, the battery capacity, the open-circuit battery voltage $V_{OC}$, the battery impedance, and/or any of the other measurements taken according to the current invention, including $V_0, V_1, V_2, I_0, I_1$, and/or $I_2$.

The various processing steps performed herein may be performed entirely by any combination of hardware, software, and/or firmware included within the IMD. Alternatively, the processing steps may be performed by any combination of hardware, software, and/or firmware provided by an external device such as a patient or clinician programmer and/or a recharge unit used to recharge a rechargeable battery. In one embodiment, circuitry within the IMD and the external device work together to perform the processing steps.

The invention may usefully employ any type of current source design, including, but not limited to, BJT current mirrors, Wilson current sources, Widlar current sources, and various types of Cascoded current sources. Moreover, the techniques described herein may be practiced using other circuits besides traditional current sources to generate the currents according to the invention. Any circuit that may be selectively activated, and that generates a stable current having a known amplitude that does not vary despite limited variations in the level of the voltage that is provided to that circuit (that is, the variations within the voltage level are within some known range of voltage variations) may be defined as a current source for purposes of the invention.

According to one aspect of the invention, a system for monitoring a battery is provided for use in an implantable medical device that contains the battery. The system includes a first current source associated with a current having a first predetermined amplitude, and a second current source associated with a current having a second predetermined amplitude. The system further includes a control circuit that is coupled to the first current source and the second current source to activate the first current source and obtain a first voltage measurement across the battery while the first current source is activated and to activate a second current source and obtain a second voltage measurement across the battery while the second current source is activated. Impedance of the battery is then determined from the first and the second predetermined amplitudes and the first and the second voltage measurements.

In one embodiment, the control circuit is adapted to determine the battery impedance from the first and the second predetermined amplitudes and the first and the second voltage measurements. In a more particular embodiment, the battery impedance is determined as (the first voltage measurement-the second voltage measurement)/(the second predetermined amplitude-the first predetermined amplitude).

According to another aspect of the invention, the system may further include a storage device to store data indicative of a characteristic of the battery. The control circuit is adapted to utilize at least one of the battery impedance and the open-circuit battery voltage to reference the data indicative of a characteristic of the battery. This data is used to determine a time until an action involving the battery is required. The action may involve activation of an ERI indicator, activation of an EOL indication, or the initiation of a recharge session.

Another embodiment relates to a method of monitoring a battery supplying power to an implantable medical device. This method includes activating a first current source that sources or sinks a current of a first predetermined amplitude, and obtaining a first voltage measurement while the first current source is activated. The method also includes activating a second current source that sources or sinks a current of a second predetermined amplitude, and obtaining a second voltage measurement while the second current source is activated. Impedance of the battery may then be determined from the first predetermined amplitude, the second predetermined amplitude, the first voltage measurement, and the second voltage measurement.

A system for monitoring a battery of an implantable medical device that is implanted in a body is also disclosed. This system includes a first current source that causes a current of a first predetermined amplitude to be drawn from the battery, and a second current source that causes a current of a second predetermined amplitude to be drawn from the battery. A measurement circuit is provided to measure a first voltage across the battery when a first combination of the first and second current sources is activated and to measure a second voltage across the battery when a different combination of the first and the second current sources is activated, whereby impedance of the battery is determined from the first predetermined amplitude, the second predetermined amplitude, the first voltage, and the second voltage. In one embodiment, the first combination includes just the first current source, and the second combination includes only the second current source. In another embodiment, the first combination includes either the first or the second current source, and the second combination includes both the first and the second current source.

Another embodiment comprises a system for monitoring a battery of an implantable medical device. First current source means are provided for causing a battery to provide a current of a first predetermined amplitude. Second current source means are provided for causing a battery to provide a current of a second predetermined amplitude. Measurement means are available for obtaining a first voltage measurement across the battery when a first combination of the first current source means and the second current source means are selectively activated, and for obtaining a second voltage measurement across the battery when a second combination of the first current source means and the second current source means is selectively activated. Control means are included for determining impedance of the battery based on the first predetermined amplitude, the second predetermined amplitude, the first voltage measurement, and the second voltage measurement.

Other scopes and aspects of the invention will become apparent from the detailed description of the drawings and the accompanying figures.

DRAWINGS

DETAILED DESCRIPTION OF THE DRAWINGS

The invention described herein relates to accurate techniques for determining battery impedance within an Implantable Medical Device (IMD) without disconnecting the battery from the circuit to which it supplies power. Battery impedance may then be employed to more accurately determine battery capacity, and a time remaining until some action must be taken involving the battery. Such actions may include, but are not limited to, activation of an ERI indicator, activation of an EOL indicator, and initiation of a recharge session.

Figure 1:
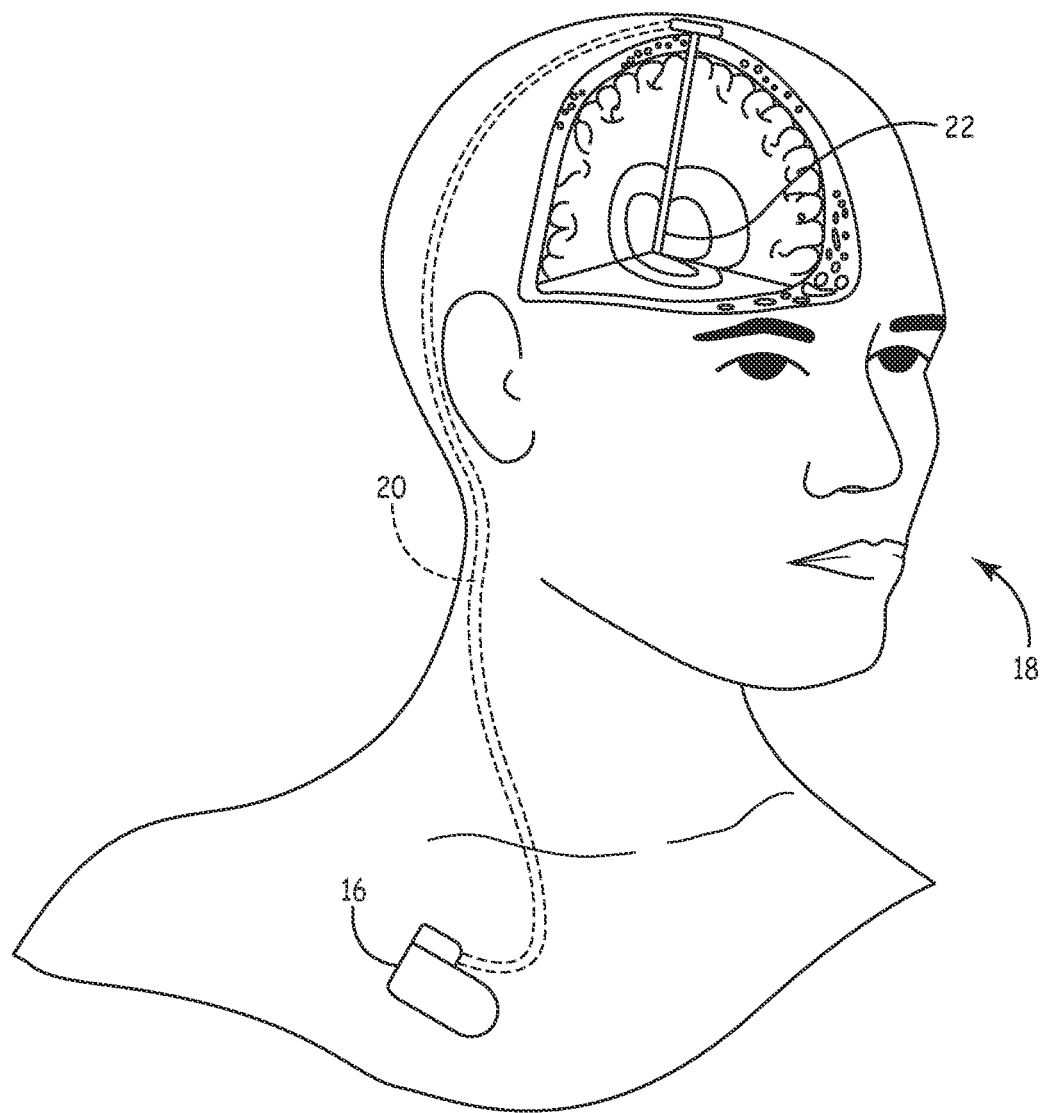
FIG. 1 is a block diagram of an exemplary Implantable Medical Device implanted in a patient.

FIG. 1 shows an exemplary IMD 16, which may be a neurostimulator, implanted in patient 18. For example, such a stimulator may be provided for the treatment of pain, epilepsy, depression, migraine headaches, gastric disorders, incontinence, sexual disfunction, dystonia, movement disorders such as Parkinson's disease and essential tremor, and other conditions. Other examples of IMDs include, but are not limited to, implantable drug infusion pumps, cardioverters, cardiac pacemakers, defibrillators, cochlear implants, and any other IMD for delivering therapy to a patient.

IMD 16 is typically implanted by a surgeon in a sterile surgical procedure performed under local, regional, or general anesthesia. One or more therapy connections 20 (shown dashed) such as leads or catheters are typically implanted with a distal end positioned at a desired therapeutic delivery site 22. In the exemplary embodiment, a proximal end of a therapy connection 20 may be tunneled under the skin to the location where IMD 16 is to be implanted.

Figure 2:
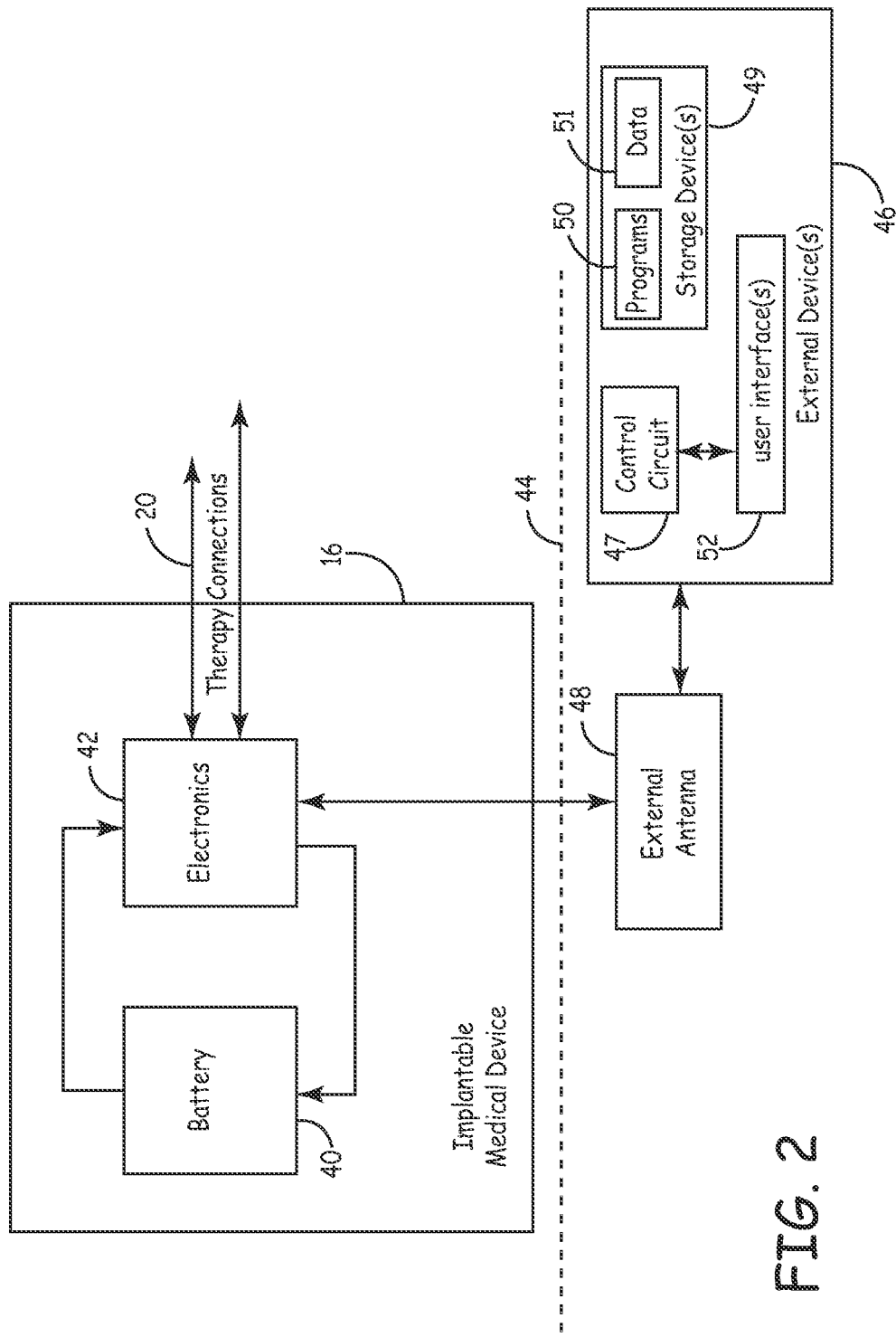
FIG. 2 is a block diagram representing the functional blocks of one embodiment of an exemplary Implantable Medical Device.

FIG. 2 is a block diagram representing one embodiment of IMD 16. The device includes a battery 40 coupled to electronics 42. Electronics 42 includes the various functional blocks of IMD 16, such as those provided to deliver therapy to the patient, sense patient conditions, communicate to the outside world, and so on. Exemplary functions provided by electronics are discussed below. Therapy delivery may be performed via therapy connections 20, which may include leads, catheters, and other connection devices coupling IMD to a patient's body.

IMD 16 is implanted in a body, and may be proximal to a cutaneous boundary 44 (shown dashed). IMD may interact with an external device 46 such as a programmer, which may be a patient or clinician programmer. Such a programmer communicates with IMD 16 via an external antenna 48, which may include a telemetry coil. The programmer may thereby establish a telemetry session with IMD to provide programs, instructions, parameters, data, and other information to IMD 16, and to likewise receive status, data, parameters, programs, and other information from the IMD. Status information received from the IMD may include data about the battery capacity that has thus far been delivered by the battery and consumed by the IMD as compared to when the battery was in the full-charged state ("battery capacity"). Status information may also include an ERI indicator to indicate when surgery must be scheduled to replace battery 40 if the battery is non-rechargeable. Status may also include an EOL indicator, which is activated to signify end-of-battery life for a non-rechargeable battery. If battery is rechargeable, the status may provide an indication as to when the next recharge session should occur so that the battery is replenished before all charge has dissipated.

If battery 40 is a rechargeable battery, external device 46 may be, or may include, a recharge unit adapted to transfer power to battery 40 across cutaneous boundary 44. In this instance, external antenna 48 includes a primary recharge coil which is positioned close to cutaneous boundary 44. When a current is generated in the primary coil, this primary coil is inductively coupled to a secondary coil that is provided by electronics 42. This current is used by electronics 42 to recharge battery 40.

External device 46 may include a control circuit 47, which may comprise one or more microprocessors, Application-Specific Integrated Circuits (ASICs), Digital Signal Processors (DSPs), Field-Programmable Gate Arrays (FPGAs), discrete electronic components, state machines, sensors, and/or other circuitry.

Control circuit 47 may operate under the control of programmed instructions such as software and/or firmware instructions stored within storage device(s) 49. Storage device(s) 49 may include volatile, non-volatile, magnetic, optical, and/or electrical media for storing digital data and programmed instructions, including Random Access Memory (RAM), Read-Only Memory (ROM), Non-Volatile RAM (NVRAM), Electrically Erasable Programmable ROM (EEPROM), flash memory, removable storage devices, and the like. These one or more storage devices may store programs 50 executed by control circuit 47. The storage device(s) may likewise store data 51 such as programmed parameters. In one embodiment, storage device(s) store battery characteristic data that is used to determine a battery capacity and/or data describing time remaining before an action must be taken relative to a battery, such as setting an ERI or EOL indicator or initiating a recharge session. This will be discussed further below.

External device(s) 46 may also include user interface(s) 52, which may include display screens, printers, devices to generate audio signals, speech-generation mechanisms, tactile feedback mechanisms such as devices that generate vibrations, and/or any other types of devices that may be used to provide feedback to a user. Such devices may be used to communicate battery status to a patient and/or clinician which may include battery impedance, open-circuit battery voltage, battery capacity, a time remaining until some action involving the battery is required, and/or information pertaining to the action that is required. This is discussed further below.

Figure 3:
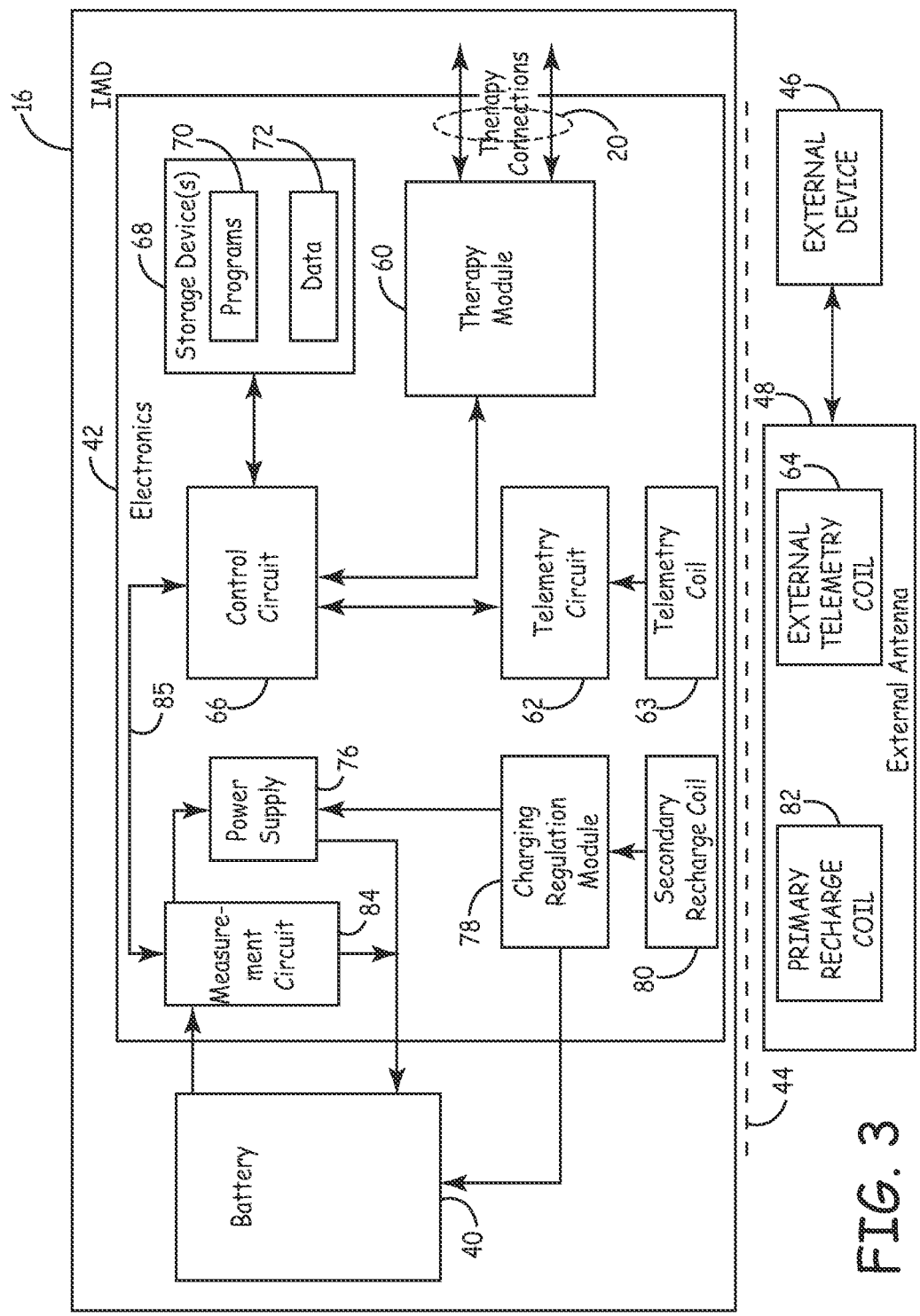
FIG. 3 is a more detailed block diagram of the electronics of one embodiment of an Implantable Medical Device.

FIG. 3 is a block diagram illustrating one embodiment of electronics 42 of IMD 16 in more detail. Electronics 42 includes a therapy module 60 which is coupled to therapy connections 20. Therapy module 60 provides one or more mechanisms and functions to deliver therapy to a patient. For instance, therapy module may include a pulse generator to deliver electrical stimulation pulses to a patient via one or more leads. Therapy module may additionally or alternatively include a drug pump to deliver agents to a patient to treat a variety of disorders including diabetes, pain, cancer, and many other types of conditions.

Electronics 42 may also include a telemetry circuit 62 which is coupled to an internal telemetry coil 63. Internal telemetry coil 63 may be electromagnetically coupled to an external, or primary, telemetry coil 64 of external antenna 48. External device 46, which may be a programmer as discussed above, may communicate with IMD 16 via external antenna 48 to transfer patient information, programs, data, parameters, and other information to the IMD via a telemetry downlink session. Conversely, IMD 16 may likewise transfer device and patient status, sensed information, and other data from the IMD to external device 46 via a telemetry uplink session.

Therapy module 60 and telemetry circuit 62 may both be coupled to a control circuit 66. Control circuit may include one or more microprocessors, ASICs, DSPs, FPGAs, discrete electronic components, state machines, sensors, and/or other circuitry. Control circuit 66 may provide control signals to therapy module 60 and telemetry circuit 62 to control operations of the system. Control circuit 66 may provide these control signals based, at least in part, on status and feedback signals received from therapy module 60 and parameters, data, programs and other information received from one or more external device(s) 46 via telemetry circuit 62.

Control circuit 66 may operate under the control of programmed instructions such as software and/or firmware instructions stored within storage device(s) 68. Storage device(s) 68 may include volatile, non-volatile, magnetic, optical, and/or electrical media for storing digital data and programmed instructions, including RAM, ROM, NVRAM, EEPROM, flash memory, removable storage devices, and the like. These one or more storage devices may store programs 70 executed by control circuit 66.

Storage devices 68 may likewise store data 72, which may include, but is not limited to, programmed parameters, patient information, data sensed from the patient, and status information indicating the status of the IMD. For instance, data 72 may include statistical information and other battery characteristic data that is used to predict charge remaining within battery 40 based on various battery measurements. Data 72 may further contain ERI and/or EOL indicators to indicate when replacement operations will be needed. In the case of a rechargeable battery, the status information may indicate an estimated time remaining before recharge of the battery will be required. This information may be provided to a clinician or patient via telemetry circuit 62, external telemetry coil 63, and external antenna 48.

Battery 40 is coupled to a power supply 76, which may include one or more capacitors and other circuit components that are adapted to provide the required current and voltage levels to the other functional blocks of electronics 42. The connections between power supply 76 and all of the other logical blocks within electronics 42 are not shown for ease of reference.

If battery 40 is a rechargeable battery, electronics may contain a charging regulation module 78 that is coupled to a secondary recharge coil 80. In this case, external antenna may include a corresponding primary recharge coil 82. External device 46, which may be, or include, a recharging unit, generates a current in primary recharge coil 82 of external antenna 48. This electro-magnetically couples primary recharge coil 82 to secondary recharge coil 80, thereby inducing a current in secondary recharge coil 80. Charging regulation module 78 employs this current to recharge battery 40, and may also provide the current to power supply 76 to power the various functional blocks of electronics 42 while a recharge session is underway.

Electronics 42 may further including a measurement circuit 84 which is coupled to the terminals of battery 40. This measurement circuit is provided to measure voltage across the terminals of the battery according to the current invention. This circuit may also have the capability to measure current flowing to electronics 42 from battery 40. This will be discussed further below.

As discussed above, it is important to be able to determine with some degree of accuracy the battery capacity that has thus far been delivered to the circuit. In the case of a non-rechargeable battery, this will determine when a replacement operation must be scheduled. For a rechargeable battery, this will indicate when a recharge session must be initiated.

One way to predict remaining charge involves measuring open-circuit voltage across the battery terminals. To accomplish this, the battery must be temporarily disconnected from the circuit that it powers, as will be discussed further below. The voltage is then measured across the battery terminals. Based on the measured voltage, statistical data may be used to predict a remaining charge existing on the battery.

In some cases, it is more accurate to utilize battery impedance rather than open-circuit battery voltage to determine battery capacity. This is the case, for instance, for those battery types such as some lithium ion batteries, wherein the open-circuit voltage characteristics exhibit a sharp drop-off as the battery nears end-of-life. For some such battery types, the impedance characteristics may exhibit a more gradual change as battery capacity is depleted. This more gradual change in impedance may provide an earlier, more accurate warning regarding capacity depletion than will the voltage characteristics.

Figure 4:
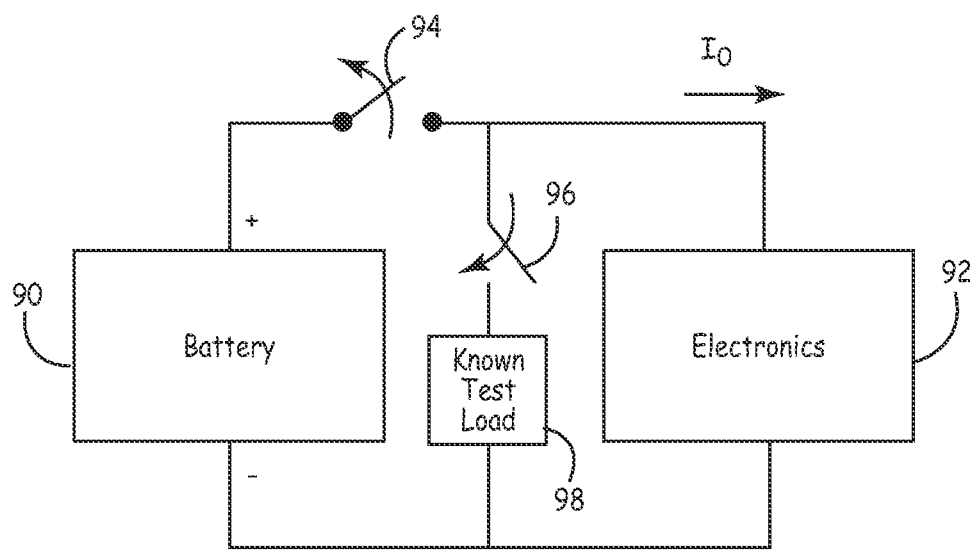
FIG. 4 is a circuit diagram of a circuit that may be used to determine battery impedance within an Implantable Medical Device.

FIG. 4 provides a circuit that may be used to determine battery impedance within an IMD. In a manner similar to that shown in FIG. 2, the system includes a battery 90 that is coupled to electronics 92. Battery 90 is coupled to electronics 92 via a programmable switch 94. Switch 94 may be controlled by a circuit such as control circuit 66 (FIG. 3). Periodically, this switch 94 may be opened so that current from the battery 90 to the circuit is interrupted. An open-circuit voltage measurement is taken across the battery terminals using a voltage measurement circuit.

Once an open-circuit voltage measurement is obtained, switch 94 may be closed. Next, a second programmable switch 96 is closed. Switch 96 allows current to flow through a known test load 98, which has a known impedance. A voltage measurement circuit is employed to measure the voltage across the known test load. Using the determined open-circuit voltage, the measured voltage across the test load, and the impedance of the known test load 98, voltage divider calculations may be employed to determine battery impedance.

The impedance measurement mechanism of FIG. 4 requires that electronics 92 be temporarily disconnected from battery 90 using switch 94. This is similar to the way open-circuit voltage is measured when open-circuit voltage is, itself, used as the measurement that determines battery capacity. Thus, in the past, regardless of whether a battery impedance or open-circuit voltage measurement was being employed to determine the battery capacity, electronics 92 had to be temporarily disconnected from the battery.

In some applications, temporarily interrupting the supply of power to the electronics is not desirable, or even possible. For example, the electronics may be part of a circuit that is sensing for one or more clinical events. Discontinuing power to the sensing circuitry, even temporarily, may cause an event to go undetected. This may not be acceptable in some applications. As another example, temporarily disconnecting the battery may result in the interruption of therapy that is being delivered to a patient, which may not be desirable or even permissible.

Even in cases wherein temporary interruption of power will not affect sensing of clinical events or delivery of therapy, the ability to allow for such a power disruption to electronics 92 complicates the circuit design. Moreover, at the very least, some alternative power source must be provided to the circuitry that is performing the open-circuit voltage measurement.

One way to address the foregoing concerns is to utilize an alternative power source to power the electronics while the battery is disconnected. For instance, a capacitor may receive a charge from battery 90. The charge from the capacitor is, in turn, used to power some, or all, of the circuitry represented as electronics 92. Battery 90 may be temporarily disconnected from the capacitor to determine the battery open-circuit voltage while the accumulated charge on the capacitor is still supplying power to electronics, and in particular, to the circuitry that will perform the open-circuit voltage measurement. In this manner, the electronics 92 need not be designed to accommodate a temporary disruption of power. However, this would require the use of a bulky capacitor that, in most cases, could not be readily incorporated into an integrated circuit. This increases the design size and complexity.

For the foregoing reasons, the mechanisms heretofore employed to measure battery impedance have been associated with disadvantages. The invention described herein eliminates this requirement through the use of current sources.

Figure 5:
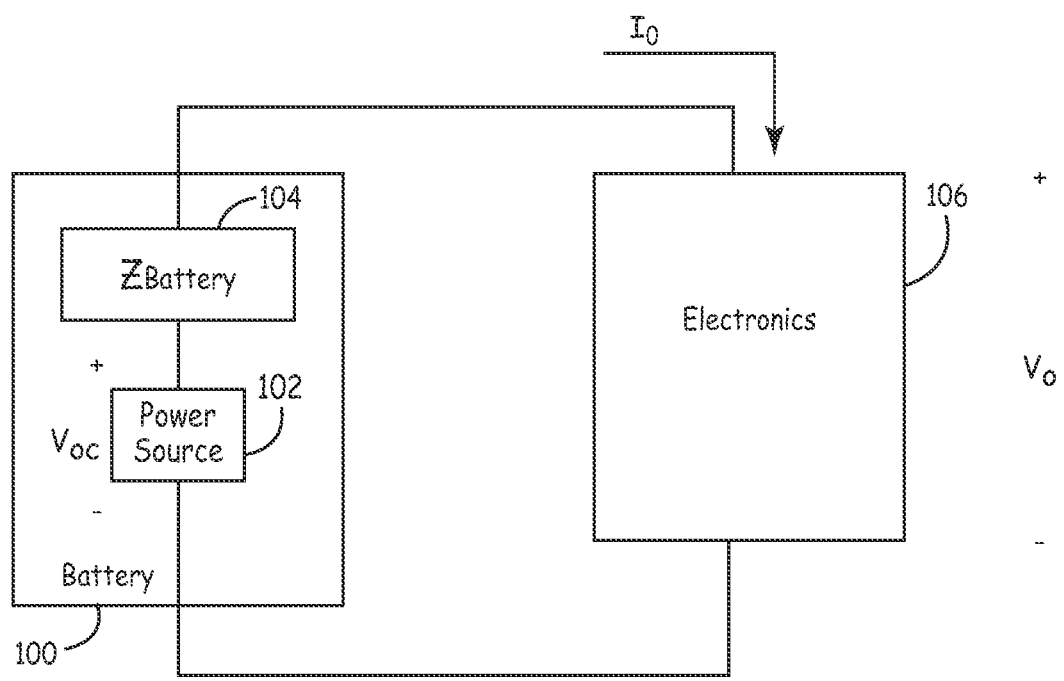
FIG. 5 is a block diagram illustrating a battery coupled to electronics of an exemplary IMD.

FIG. 5 is a block diagram illustrating a battery 100 coupled to electronics 106, which may be electronics included within an exemplary IMD. This diagram is used to describe a circuit model that may be employed to represent battery 100. Battery 100 has some internal battery impedance, $Z_{BATTERY}$. Battery 100 may therefore be represented as a power source 102 that is electrically coupled in series with an impedance of $Z_{BAT}$ TERY, 104. A voltage exists across the power source 102. This is the open circuit voltage, or $V_{OC}$, that could be measured across the terminals of battery if no current were being drawn from the battery. In particular, $V_{OC}$ may be determined by opening a switch such as switch 94 (FIG. 4) and measuring the voltage across the battery terminals in the manner discussed above. However, as previously described, obtaining this type of measurement requires temporarily disconnecting electronics 106 from battery 100, something that is undesirable or even impermissible in some designs.

As mentioned above, the battery has a battery impedance, $Z_{BATTERY}$, which is modeled by block 104. The battery impedance cannot be readily directly measured when the battery is contained within an implanted IMD. This battery impedance will vary depending on the charge remaining on battery 100, and will also generally vary from battery to battery because of component tolerances.

Electronics 106 draw some current from battery 100. This current will vary depending on the operations being performed by the electronics at a given point in time. For instance, electronics will likely draw more current when therapy is being delivered to a patient and/or when a communication session is underway, as via telemetry circuit 62 and telemetry coil 63 (FIG. 3). At other times, when therapy is not being delivered, a communication session is not occurring, and no other intermittent function that draws a sizeable current is occurring, it will be assumed that electronics 106 draws a passive or quiescent current $I_0$. This quiescent current will have a relatively constant amplitude of $I_0$ for a given device. However, this amplitude is generally difficult to predict for a given instance of a device, and therefore is generally an unknown parameter. This is for at least the reason that the quiescent current amplitude will vary between device instances based on tolerances of the components included within electronics 106.

As shown in FIG. 5, when electronics 106 are drawing a passive current $I_0$, a voltage of $V_0$ exists across the electronics.

The various parameters shown in FIG. 5 have the following relationship:

$$V_{OC} = V_0 + (I_0 \times Z_{BATTERY})$$

While $V_0$, which is the voltage across electronics 106, may be measured using a circuit such as measurement circuit 84 (FIG. 3) in a manner to be discussed below, the remaining values are unknown. Thus, one cannot solve for either $Z_{BATTERY}$ or $V_{OC}$ using this relationship. Thus, heretofore, without disconnecting the battery from electronics of an implanted IMD, it has not been possible to obtain the battery characteristics needed to predict the delivered battery capacity or the battery capacity that remains to be delivered.

The current invention remedies the deficiencies of the prior art by incorporating current sources into the system so that the battery capacity may be determined without the need to temporarily disrupt power delivery to an IMD. This is discussed in reference to the remaining drawings.

Figure 6:
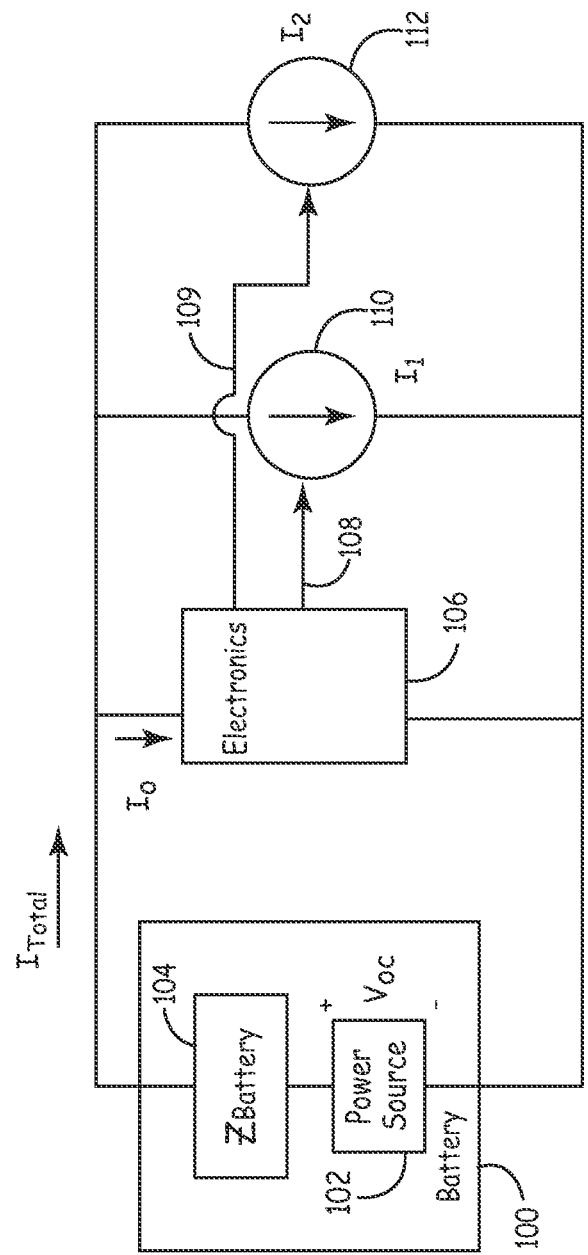
FIG. 6 is a circuit diagram illustrating a circuit employed to determine battery impedance according to one embodiment of the current invention.

FIG. 6 is a circuit diagram illustrating one embodiment of the present invention. According to this embodiment, a first current source 110 is provided to generate a first current having a known amplitude of $I_1$. A second current source 112 is also provided to generate a second known current having an amplitude of $I_2$.

A current source is a circuit that either sources or sinks a current having a constant amplitude despite variances in voltage across the current source. In practice, so long as the voltage supplied to the current source stays within some predetermined specified voltage range associated with the given current source design, the current generated or absorbed by the current source will remain constant.

Current sources typically include small components that may readily be incorporated into a circuit design, such as the circuit design of an IMD. Exemplary current source designs are discussed below.

First and second current sources 110 and 112 may each be selectively enabled by electronics 106, as may occur via control lines 108 and 109, respectively. For instance, these control lines may be activated via a circuit such as control circuit 66 (FIG. 3). When a current source is activated by electronics, the current source provides a current of the predetermined known amplitude. As discussed above, even when the voltage across the battery begins to diminish as the battery capacity is being used and charge is depleted, the amplitude of the generated current will be a known value. When a current source is not activated because a corresponding control line has been disabled, the current source acts as an open circuit that does not draw current and does not affect the electrical characteristics of electronics 106 or battery 100.

The circuit of FIG. 6 may be employed to very accurately measure the impedance of the battery without the need to determine the amplitude of the quiescent current and without the need to disconnect the battery from the circuit to which it supplies power as follows. During a time when electronics 106 are known to be in a passive state such that the electronics are drawing the quiescent current having an amplitude of $I_0$, a programmably-controlled circuit within electronics 106 such as control circuit 66 (FIG. 3) activates control line 108 to enable a first combination of the first and second current source. For purposes of this example, this first combination will include only the first current source 110. When this occurs, the total current being drawn from battery 100 is known to be a sum of the quiescent current having an amplitude of $I_0$ and the predetermined current that is associated with (that is, either sourced or sunk by) current source 110, which has an amplitude $I_1$. While the total current is being drawn from battery 100, a circuit such as measurement circuit 84 (FIG. 3) measures the voltage $V_1$ across the terminals of battery 100, which is also the voltage across electronics 106.

The relationship between currents, the measured voltage $V_1$, open circuit battery voltage $V_{OC}$, and battery impedance $Z_{BATTERY}$ is as follows:

$$V_1 = V_{OC} - Z_{BATTERY}(I_0 + I_1)$$

That is, the voltage measured across the terminals of the battery is the open circuit voltage less the voltage drop that occurs because of the battery impedance, which is $Z_{BATTERY}$ multiplied by the total current comprising the quiescent current having an amplitude of $I_0$ and the current sourced by current source 110, which has an amplitude of $I_1$.

Next, in one embodiment, control line 108 is deactivated. While electronics 106 is still drawing the quiescent current $I_0$, the programmably-controlled circuit within electronics 106, which may be a circuit such as control circuit 66 (FIG. 3), activates control line 109 to enable a second combination of the first and second current source. This second combination is different from the first combination. For purposes of this example, the second combination includes only the second current source 112. At this time, the amplitude of the total current being drawn from battery 100 is known to be a sum of the amplitude of the quiescent current $I_0$ and the current associated with (that is, either sourced or sunk by) second current source 112. While this current is being drawn from the battery 100, a circuit such as measurement circuit 84 measures the voltage $V_2$ across the terminals of battery 100, which is also the voltage across electronics 106.

The relationship existing between various currents, the measured voltage $V_2$, the open circuit battery voltage $V_{OC}$, and the battery impedance $Z_{BATTERY}$ is as follows:

$$V_2 = V_{OC} - Z_{BATTERY}(I_0 + I_2)$$

That is, the voltage measured across the terminals of the battery is the open circuit voltage less the voltage drop that occurs because of the battery impedance $Z_{BATTERY}$ multiplied by the total current amplitude of $I_0 + I_2$.

The two relationships described above may be summarized as follows:

$$V_1 = V_{OC} - Z_{BATTERY}(I_0 + I_1)$$

$$V_2 = V_{OC} - Z_{BATTERY}(I_0 + I_2)$$

These relationships may be manipulated as follows:

$$V_1 - V_2 = [V_{OC} - Z_{BATTERY}(I_0 + I_1)] - [V_{OC} - Z_{BATTERY}(I_0 + I_2)]$$

Battery impedance can therefore be expressed as $$Z_{BATTERY} = (V_1 - V_2)/(I_2 - I_1)$$

In the foregoing manner, the battery impedance may be derived using the known values of the current amplitudes, $I_1$ and $I_2$, and the measured voltages $V_1$ and $V_2$. This may be accomplished without the need to temporarily disconnect battery 100 from electronics 106 and without the need to know the amplitude of the quiescent current $I_0$.

The above-described embodiment assumes that $I_1$ and $I_2$ have different amplitudes. However, this need not be the case. For instance, in one embodiment, $I_1$ and $I_2$ have the same amplitudes. A first set of measurements is taken with either one of the current sources 110 or 112 activated. A second set of measurements may then be taken with both current sources activated. According to this alternative embodiment, the first combination of the first and the second current sources that are activated includes either one of the current sources. The second combination of the first and the second current sources to be activated includes both current sources.

The impedance may then be calculated as follows:

$$Z_{BATTERY} = (V_1 - V_2)/(I_1) = (V_1 - V_2)/(I_2)$$

In one embodiment of the invention, a measurement circuit such as measurement circuit 84 (FIG. 4) is included in electronics 106 to sample the quiescent current $I_0$. For example, this circuit may include a resistor having a known resistance that may be switched into series with electronics 106. The voltage existing across the resistor may be measured and the amplitude of the quiescent current $I_0$ may be determined by dividing the measured voltage by the known resistance.

Once the quiescent current $I_0$ has been determined, the open-circuit battery voltage may be calculated as follows:

$$V_{OC} = V_0 + (I_0 \times Z_{BATTERY})$$

This calculation utilizes the voltage measurement $V_0$ that is obtained across the battery terminals when both current sources 110 and 112 are deactivated and electronics are only drawing the quiescent current $I_0$. In this manner, the open circuit voltage may be obtained without the need to disconnect the battery from electronics 106.

Figure 7:
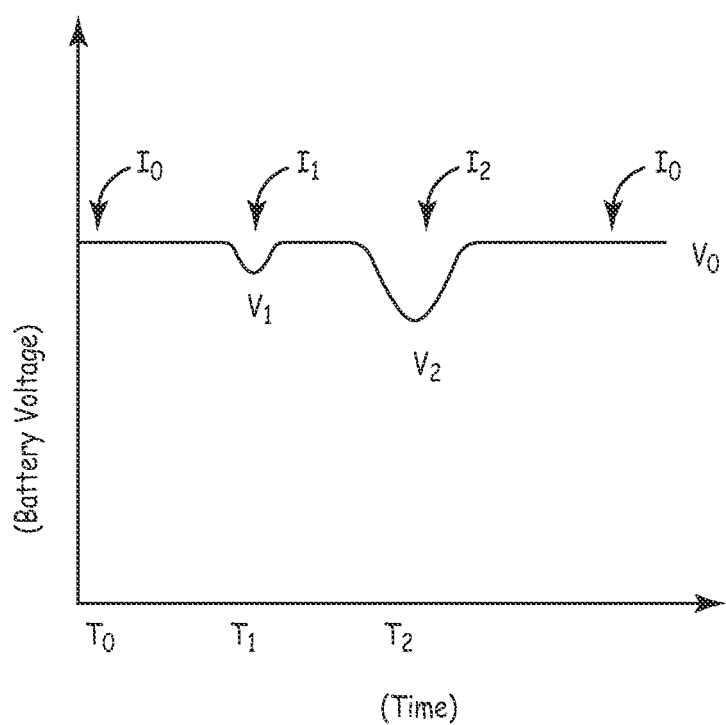
FIG. 7 is a waveform diagram that illustrates current and voltage relationships of a battery according to one embodiment of the current invention.

FIG. 7 is a waveform diagram that illustrates current and voltage relationships as the various measurements described above are taken according to one embodiment of the invention. When electronics 106 are in the passive state at time $T_0$, a voltage of $V_0$ exists across the battery terminals when the quiescent current having an amplitude of $I_0$ is being drawn by electronics. At time $T_1$, the first current source 110 is activated. This causes the voltage across the battery terminals to "dip" to the measured value of $V_1$ when the current having the predetermined amplitude of $I_1$ is sourced by the first current source. The first current source is deactivated for a period of time, followed by activation of the second current source 112 at time $T_2$. When the second current source provides the known current having an amplitude of $I_2$, the voltage across the battery terminals diminishes to the measured voltage of $V_2$. Current source 112 is then deactivated and the battery voltage returns to $V_0$ with a quiescent current of $I_0$ being drawn from the battery.

Once an accurate impedance measurement has been obtained, the impedance characteristics of the battery may be referenced to determine the battery capacity that has already been used, Q, and/or to obtain a prediction of the battery capacity that remains to be delivered by the battery. In the case of a non-rechargeable battery, this determination as to battery capacity that has been used may then be employed to determine the estimated time until ERI and/or EOL. In the case of a rechargeable battery, the battery capacity that has been used may be employed to determine when a recharge session must be initiated.

Figure 8:
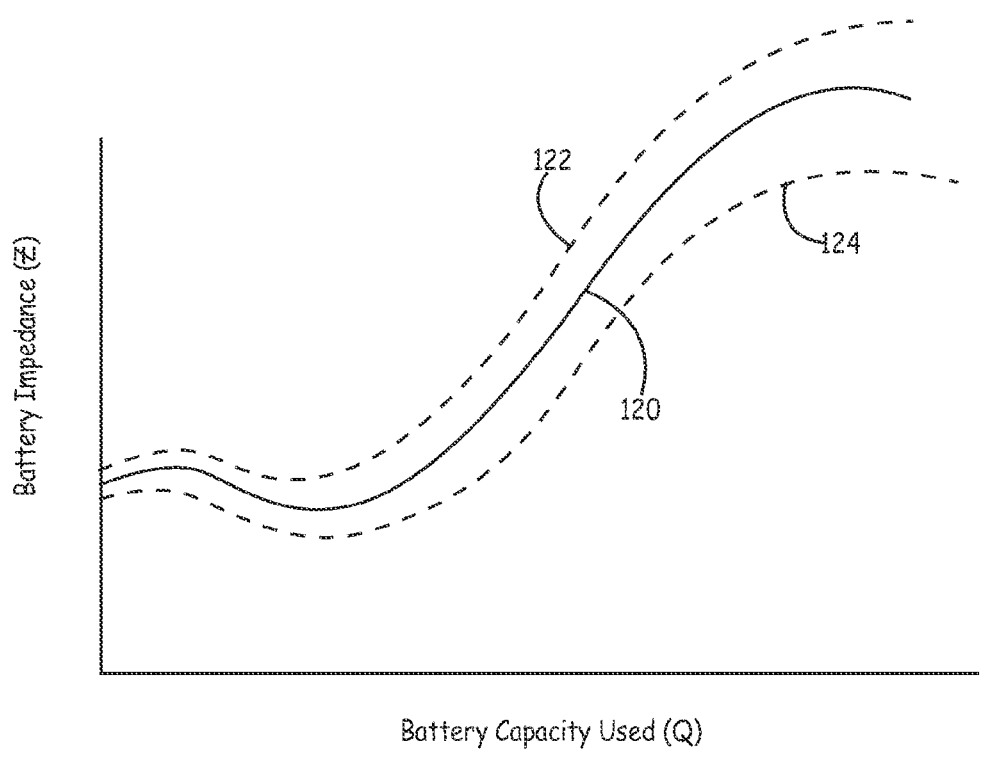
FIG. 8 is waveform diagram depicting exemplary relationships between battery impedance and battery capacity.

FIG. 8 is an exemplary waveform diagram that represents an illustrative relationship between battery impedance and the battery capacity that has been used, Q. Battery impedance Z begins to rise steadily as the battery capacity increases. That is, the battery impedance rises as the battery nears the time ERI is to be activated for a non-rechargeable battery, and as the time for scheduling a recharge session approaches in the case of a rechargeable battery.

A waveform such as that shown in FIG. 8 may take into account variations between batteries. For instance, the battery capacity for an average battery having a given impedance may be represented by waveform 120. Waveform 122 (shown dashed) may be provided to represent the same information for a battery in the fifth percentile of a statistical distribution, and waveform 124 may be provided to represent this information for a battery in the ninety-fifty percentile of the distribution.

As discussed above, based on the information obtained from the waveform of FIG. 8, an estimate may be made regarding when some action must occur involving the battery. This action may include activation of an ERI or EOL indication for a non-rechargeable battery or the initiation of a recharge session for a rechargeable battery.

The prediction as to how much time remains before some an action must occur may be based on an additional relationship that has been developed to correlate battery capacity and the time before action is required. This additional relationship may be developed empirically, for instance. The relationship may be expressed as a waveform such as that shown in FIG. 8. Alternatively, the relationship may be expressed via one or more tables or using any other appropriate data structures or mechanisms that are capable of correlating battery capacity and the remaining time before action is required.

The relationship between battery impedance and battery capacity as shown in FIG. 8, and any additional relationship correlating battery capacity to remaining time-to-action, may be stored as data 72 within storage device(s) 68 of IMD 16. Alternatively or additionally, such relationships may be stored as data 49 of external device(s) 46.

Using information obtained in the foregoing manner, a user may be provided with an estimation of the time remaining until a recharge session must be initiated for a rechargeable battery, the time remaining until ERI and/or EOL is activated for a non-rechargeable battery, or the time until some other action involving the battery will be needed or will occur. If desired, this estimation may take into account statistical variations. For instance, if the patient or a clinician desires to be conservative, the estimation may be based upon a curve such as curve 122 (FIG. 8), which represents a worst-case scenario. If more room for error exists because an IMD powered by the battery is not providing life-sustaining support, a patient or clinician may instead choose to base the estimate on a curve such as curve 124, which represents a best-case scenario.

Figure 9A:
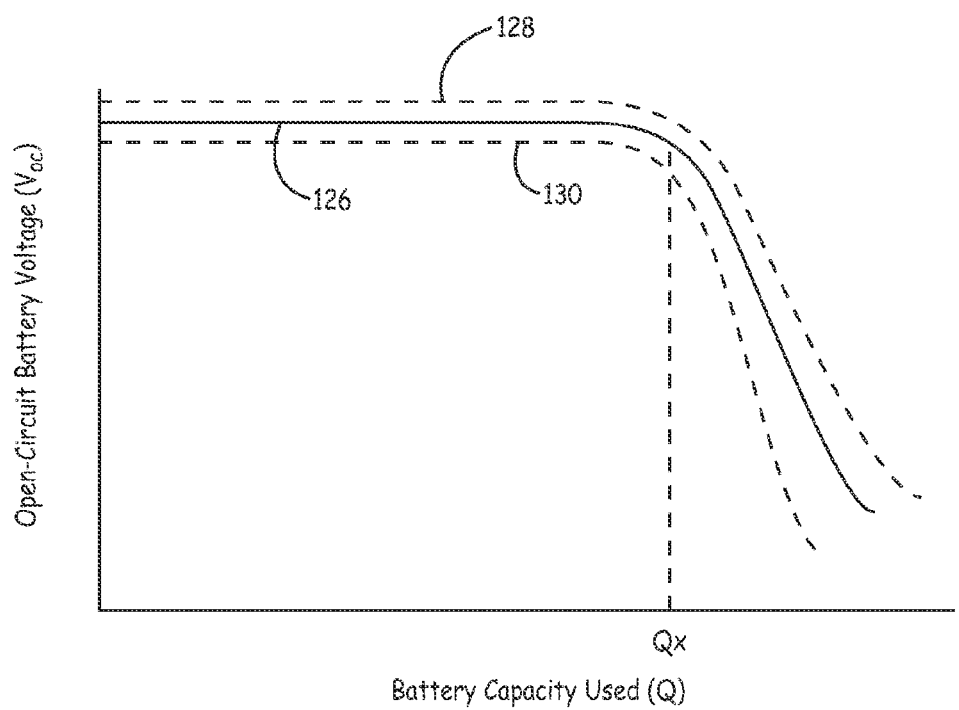
FIG. 9A is waveform diagram depicting exemplary relationships between open-circuit battery voltage and battery capacity.

FIG. 9A is an exemplary waveform diagram that represents an illustrative relationship between open-circuit battery voltage, $V_{OC}$, and the battery capacity that has been depleted thus far from the battery. In the exemplary case, the open-circuit battery voltage remains substantially constant as the battery capacity that has been depleted increases. As the battery nears the point where the charge $Q_X$ has been delivered by the battery, open-circuit voltage begins to drop. For some types of batteries, this drop may be quite steep. In other types of batteries, the drop-off may be more gradual.

The open-circuit battery voltage may be calculated in the manner described above and compared against a waveform such as that shown in FIG. 9A. Using a waveform such as shown in FIG. 9A, the battery capacity that has been used, Q, may be estimated. From this estimation, a time remaining until some action will be required (e.g., time to activation of ERI, time to EOL, or time to recharge) may be determined in any of the ways discussed above.

As was the case in FIG. 8, a waveform such as that shown in FIG. 9A may take into account variations between batteries. For instance, the charge capacity that has been used on an average battery having a given open-circuit voltage may be represented by waveform 126. Waveform 128 (shown dashed) may be provided to represent the same information for a battery in the fifth percentile of a statistical distribution, and waveform 130 may likewise be provided to represent a battery in the ninety-fifty percentile of the distribution.

Figure 9B:
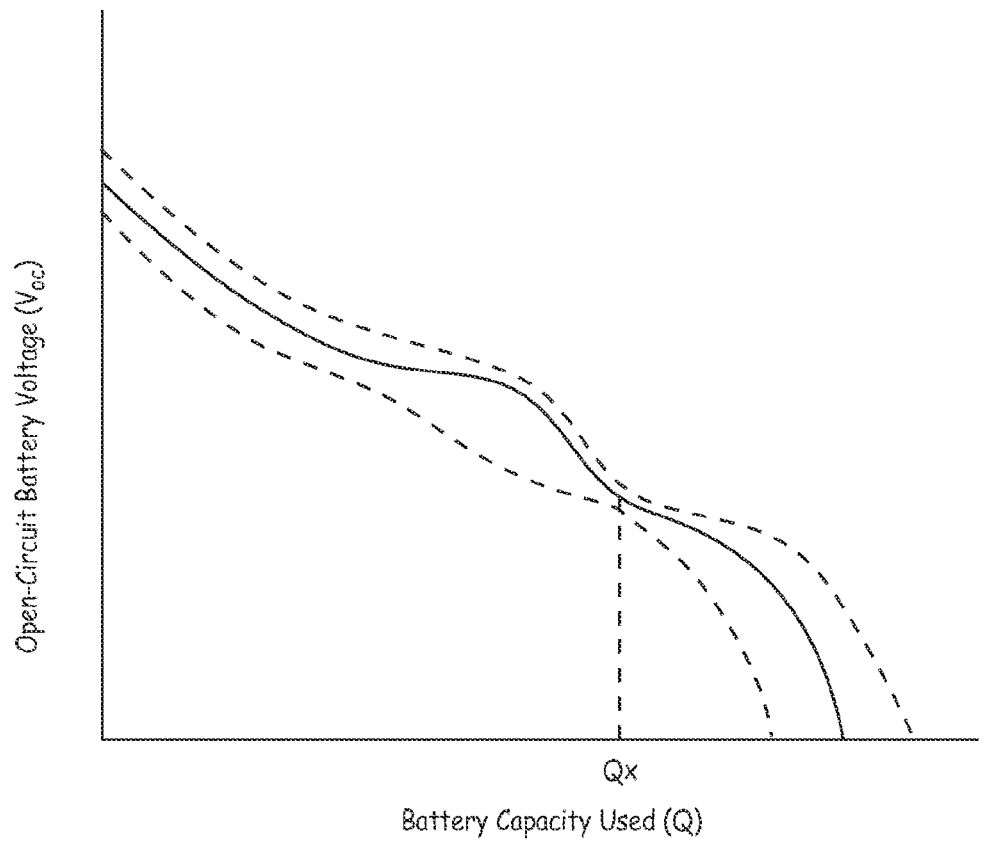
FIG. 9B is another waveform diagram depicting exemplary relationships between open-circuit battery voltage and battery capacity.

FIG. 9B is another exemplary waveform diagram that represents an illustrative relationship between open-circuit battery voltage, $V_{OC}$, and the battery capacity that been delivered so far, Q. Unlike the waveform of 9A wherein open-circuit battery voltage remains relatively constant until battery capacity reaches $Q_X$, this waveform reflects a more gradual decrease in open-circuit voltage as battery capacity is used. This will allow open-circuit voltage to be more usefully employed to determine battery capacity. As was the case in FIG. 9A, statistical distribution data may be included within the diagram, as is represented by the waveforms that are shown dashed.

It may be desirable to utilize both battery impedance and open-circuit battery voltage to determine battery capacity Q that has been delivered thus far by the battery. For instance, after both battery impedance and open-circuit battery voltage values are obtained according to the current invention, battery characteristic data such as is represented by the waveforms of FIGS. 8 and 9A or 9B, respectively, may be used to determine respective estimations of battery capacity. The two values for battery capacity may then be processed in some predetermined manner to obtain a single value representative of battery capacity. For instance, the two values may be averaged. Alternatively, one value may be discounted entirely if it is within a certain range. For example, if the open-circuit battery voltage is within a voltage range that corresponds to a relatively constant portion of the voltage/battery capacity relationship (i.e., the value corresponds to the "flat" portion of a open-circuit battery voltage waveform of the type shown in FIG. 9A), that battery voltage may be disregarded since it may not provide useful information concerning the battery capacity. In still other cases, a weighted average may be calculated from two different capacity values. Many other ways of processing of two differing battery capacity values may be used to obtain a single capacity value that is then employed to estimate a time until some action must be taken involving the battery.

Figure 10:
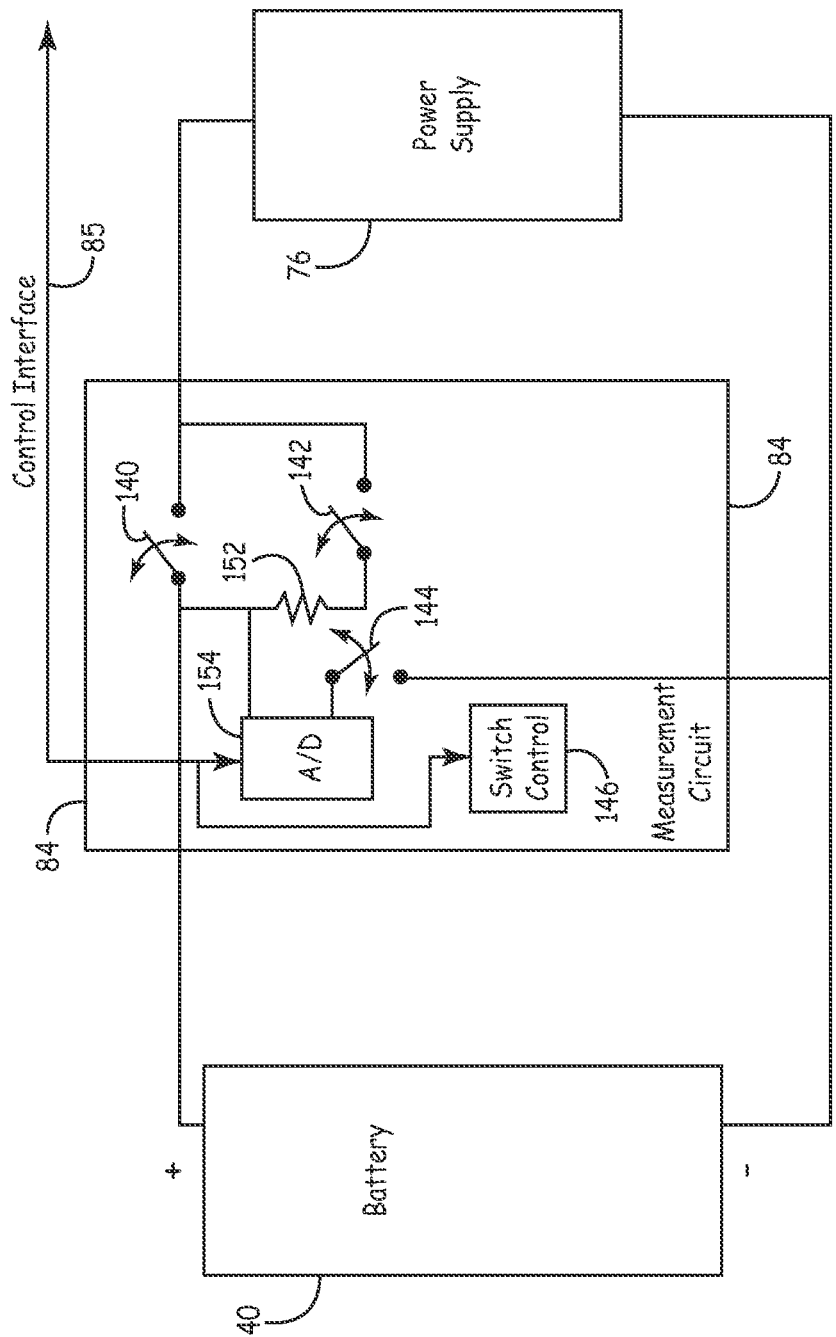
FIG. 10 is a circuit diagram illustrating an exemplary circuit that may be used to obtain current and voltage measurements according to one embodiment of the invention.

FIG. 10 is a circuit diagram of measurement circuit 84 of FIG. 3. This circuit, which may likewise be included within electronics 106 of FIG. 6, may be employed to measure voltage across terminals of battery 100 while a current is being drawn from the battery. This circuit may also be used to measure a current that is being provided by battery 100 to electronics 106. As discussed above, this capability may be used to determine the amplitude of the quiescent current, $I_0$, that is being drawn by electronics 42 for use in calculating the open-circuit voltage, $V_{OC}$, without disconnecting the battery from electronics. This circuit is also used to measure voltages $V_1$ and $V_2$ that are used in the manner discussed above.

Measurement circuit 84 includes three programmable switches 140, 142, and 144. These switches are controlled via control signals received from a control circuit such as control circuit 66 (FIG. 3) on control interface 85. These signals are provided to switch control circuitry 146, which uses the signals to control the state of the programmable switches 140, 142, and 144. The interconnections between switch control circuitry 146 and the switches are not shown for ease of reference.

Normally, programmable switch 140 is in a closed position, programmable switch 142 is in an open position, and switch 144 is in a position that connects analog-to-digital (A/D) converter 154 to the negative terminal of battery 40. While configured in this manner, the voltage across the battery may be measured by A/D converter 154 and a digital representation of this voltage may be provide via interface 85 to control circuit 66 (FIG. 3). In this manner, the voltages $V_0$, $V_1$, and $V_2$ may be obtained.

Before the quiescent current is to be measured, control circuit 66 may actively cause therapy module 60 to discontinue therapy delivery, any communication sessions, and other intermittent activities that draw a sizeable current. Alternatively, control circuit 66 may wait until a time when none of these activities is occurring. Control circuit then provides control signals on interface 85 to switch control 146. In response, switch 142 is closed and switch 140 is opened so that resister 152 is now connected in series with battery 40 and power supply 76. During this time, power continues to be delivered to power supply 76 and the rest of the circuit, which may include all of the electronics 42 shown in FIG. 3. Finally, the position of switch 144 is adjusted such that A/D converter 154 is connected across resistor 152.

After the switches have been re-positioned in the foregoing manner, A/D converter 154 is able to measure the voltage across resister 152, which has a known resistance value. A/D converter provides a digital representation of the measured voltage to control circuit 66 via control interface 85. This value may, in turn, be provided to a control circuit 47 of one or more external device(s) 46, such as via a telemetry uplink session. Control circuit 66 of IMD 16 and/or control circuit 47 of external device(s) 46, may then divide the measured voltage by the known resistance of resistor 152 to obtain the quiescent current amplitude, $I_0$. Thereafter, switch 144 may be re-connected to the negative terminal of battery in preparation for another voltage measurement, switch 140 may be closed, and switch 142 may be opened.

Because quiescent current has a relatively constant amplitude $I_0$ that does not depend on battery capacity, but rather on the tolerances of the various components included within electronics of the IMD, it is not necessary to re-measure this amplitude each time $V_{OC}$ is derived. As discussed above, this value may be measured once and stored within one or more storage devices, such as storage device(s) 68 within IMD 16, and/or storage devices 49 within external device(s) 46. This value may then be recalled to perform processing according to the current invention.

While the foregoing discussion relates primarily to FIG. 3, it will be understood that measurement circuit 84 may likewise be incorporated into the circuit of FIG. 6 for use in obtaining measurements according to the current invention.

The measurement circuit of FIG. 10 is merely exemplary, and many other measurement systems and methods are possible within the scope of the invention. For example, if desired, resistor 152 may be connected in series in a hardwired manner between battery 40 and power supply 76, with hardwired connections being provided from this resistor to A/D converter 154. In this manner, no reconfiguration of switches is needed to allow the voltage across the resistor to be measured. In a similar manner, a second set of hardwired connections may connect A/D converter 154 across terminals of battery 40 so that no switch configuration is needed to obtain the voltage across battery 40. In such a configuration, all of the switches 140, 142, and 144, as well as switch control 146, may be eliminated.

In yet another embodiment, two A/D converters may be provided, with one being hardwired across the terminals of the battery, and the second A/D converter being hardwired across resistor 152. Thus, many alternatives are available for use as measurement circuit 84.

Figure 11B:
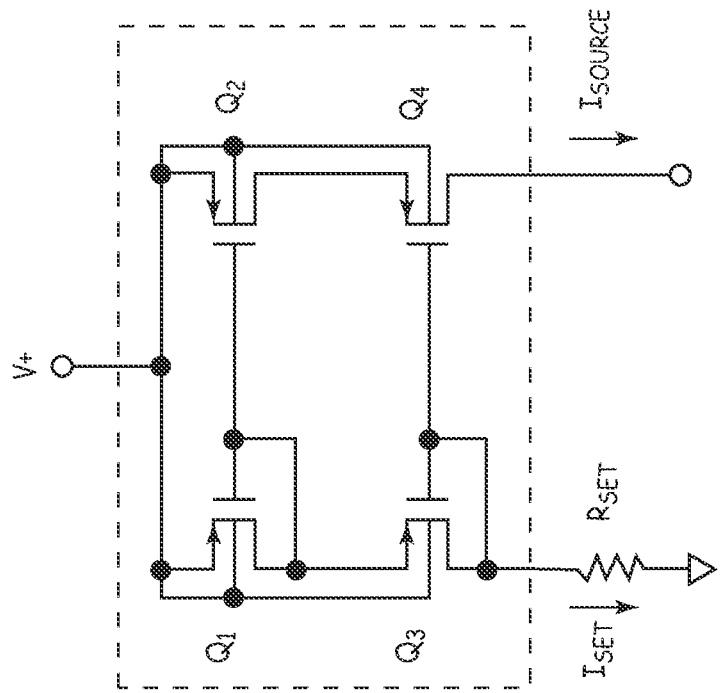
FIGS. 11A and 11B are circuit diagrams of exemplary embodiments of current sources that may be employed according to the current invention.
Figure 11A:
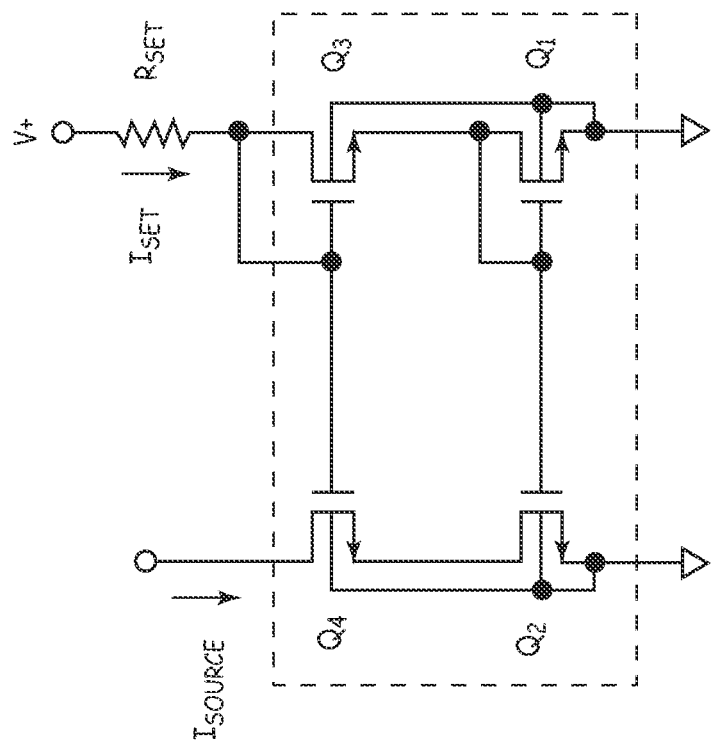

FIG. 11A is a circuit diagram of one embodiment of a current source that may be used according to the current invention. The circuit includes four N channel MOSFET transistors, Q1-Q4. The set current $I_{SET}$ will be some function of V+, as well as the gate-to-drain voltages of transistors Q1 and Q3, and the value of resistor $R_{SET}$, and thus will be dependent on the values selected for V+ and $R_{SET}$, and the types of transistors selected for use in the circuit. The amplitude of the current that is sourced, $I_{SOURCE}$, will either be equal to, or will be some known multiple of, $I_{SET}$ for a range of output voltages that is a function of the characteristics of the transistors selected. In one particular embodiment, $I_{SOURCE}$, will be equal to $I_{SET}$ so long as the output voltage exceeds the sum of the gate-to-drain voltages of transistors Q1 and Q3.

It may be desirable to configure current sources 110 and 112 such that $I_{SOURCE}$, will be a known multiple of $I_{SET}$. This will minimizing that drain on the battery 100 while providing voltages $V_1$ and $V_2$ that are easily measurable. Similar, it may be desirable to configure the current source so that V+ is smaller than the voltage delivered by battery 100, which will also limit power drawn from the battery. This configuration may be accomplished through the selection of the $R_{SET}$ value as well as the selection of the types of transistors Q1-Q4.

FIG. 11B is a circuit diagram of another exemplary current source. This circuit utilizes four P channel, rather than N channel, MOSFET transistors, Q1-Q4. As is the case for the circuit described in reference to FIG. 11A, the set current $I_{SET}$ will be determined as a function of transistor characteristics, V+, and the value selected for $R_{SET}$. $I_{SOURCE}$ will track, or will be a known multiple of, $I_{SET}$ so long as the output voltage is within a specified range of voltages that will also depend upon the selection of transistors.

Many other types of current source designs are available for use with the current invention, including, but not limited to, BJT current mirrors, Wilson current sources, Widlar current sources, and various types of Cascoded current sources. Moreover, the techniques described herein may be practiced using other circuits besides traditional current sources to generate the currents according to the invention. Any circuit that generates a stable current having an stable, known amplitude that does not vary despite variations in the voltage provided to that circuit (within some known range of voltage variations) may be employed as a current source, and will be considered a current source for purposes of the invention. Those illustrated herein are understood to be merely exemplary. Any current source having a physical size suitable for use in an IMD and that supplies a constant current over voltage ranges associated with the battery employed by the IMD may be usefully employed by the current invention.

Figure 12:
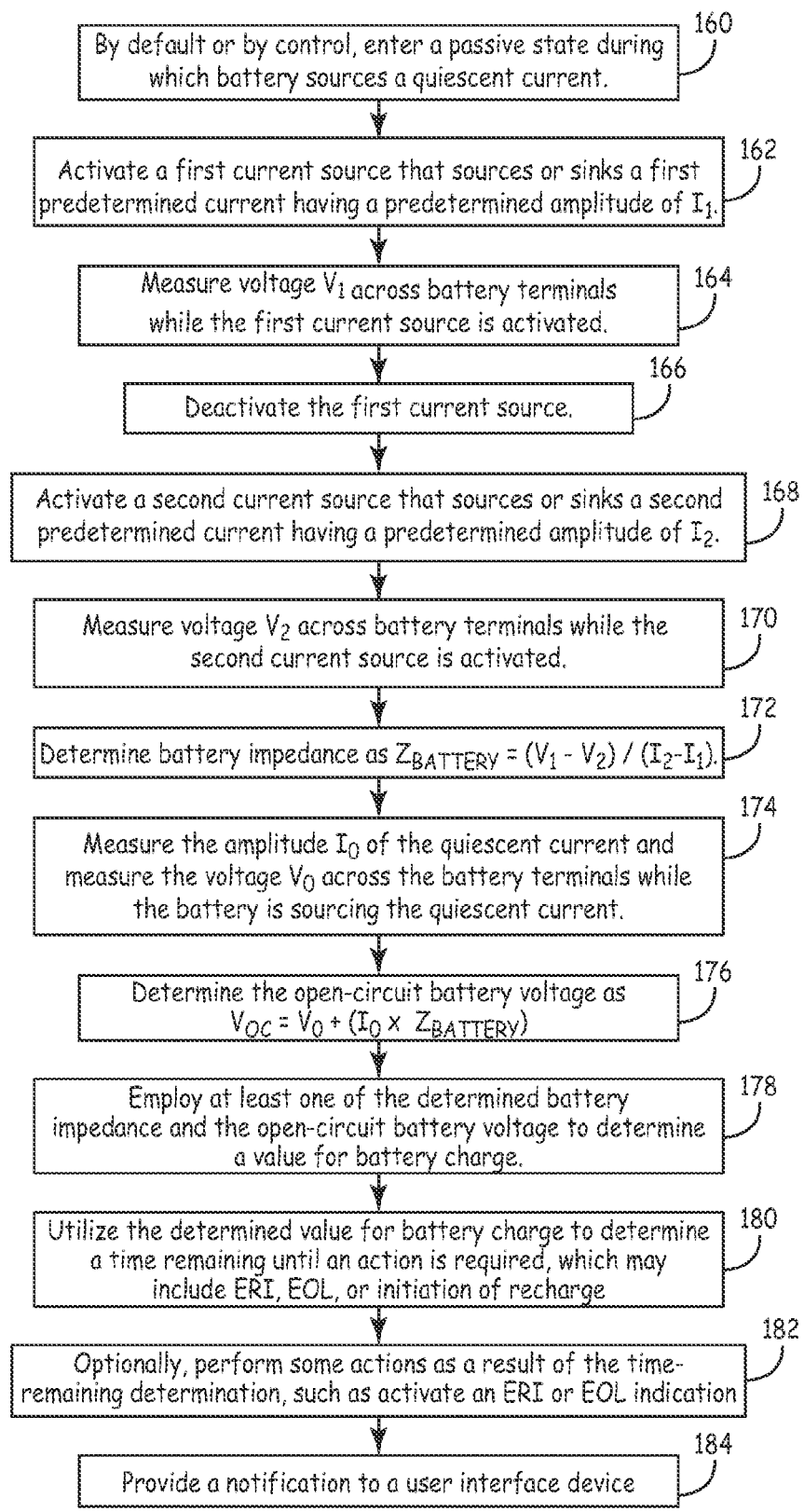
FIG. 12 is a flow diagram illustrating one method according to the current invention.

FIG. 12 is a flow diagram illustrating one method according to the current invention. In step 160, the IMD enters a passive or quiescent state during which the battery is providing a passive or quiescent current having an amplitude of $I_0$. As discussed above, a passive state is a state wherein therapy is not being delivered to a patient, a communication session is not underway, and no other intermittent function is occurring that draws any sizeable amount of current. The passive state may be entered by default between periods of time when those types of functions are not occurring. Alternatively, this passive state may be entered under the control of a circuit such as control circuit 66 (FIG. 3), which directs those types of functions to cease so that battery impedance may be determined.

Once the passive state is entered, a first current source is selectively activated (162). This current source either sources or sinks a current having a predetermined known amplitude of $I_1$. While this is occurring, a voltage $V_1$ is measured across the terminals of battery (164). Next, the first current source is deactivated (166). A second current source is selectively activated that sources or sinks a second current having a predetermined amplitude of $I_2$ (168). Voltage across the battery terminals is measured while the second current source is activated (170).

Next, in step 172, the battery impedance is determined as follows:

$$Z_{BATTERY}=(V_1-V_2)/(I_2-I_1)$$

If desired, the amplitude of the quiescent current $I_0$ may next be measured, along with the voltage $V_0$ across the battery terminals while the battery is sourcing this quiescent current (174). As discussed above, this may be accomplished using a circuit such as that illustrated in FIG. 10. Many other types of circuits may be used in the alternative.

In one embodiment, the current measurement obtained in step 174 need only be obtained once. That is, once the quiescent current amplitude $I_0$ is calculated a first time to determine open-circuit voltage, this value may simply be saved within a storage device such as one or more of storage devices 49 and 69 and recalled as needed for future use. This is because the quiescent current amplitude is not dependent on battery capacity, and will remain constant for a given instance of an IMD.

In step 176, the open-circuit voltage of the battery may then be determined using the quiescent current amplitude and the derived impedance, as follows:

$$V_{OC}=V_0+(I_0 \times Z_{BATTERY})$$

Next, at least one of the battery impedance, $Z_{BATTERY}$, and the open-circuit battery voltage, $V_{OC}$, are used to refer to battery characteristic data for the specific type of battery so that battery capacity may be determined (178). Such battery characteristic data may be derived empirically based on measurements made on multiple batteries that are of the same battery type as that which is powering the IMD. This data may be provided in graphical format as exemplified in FIGS. 8, 9A and 9B discussed herein. Alternatively, this type of data may be presented in tabular or some other format. Some or all of this data may reside as data 72 within storage device(s) 68 of an IMD, such as IMD 16 (FIG. 3). Alternatively or additionally, some or all of this data may reside as data 51 within storage device(s) 49 of an external device 46 (FIG. 2).

As may be appreciated, if both the battery impedance and the open-circuit battery voltage are used to obtain a respective value for battery capacity, some processing may be needed to obtain a single value that represents battery capacity. For instance, an average, which may be a weighted average, may be obtained from the multiple battery capacity values. Alternatively, one of the battery capacity values may be disregarded entirely. Other mechanisms may be used to obtain a single battery capacity value from multiple values.

Next, the battery capacity value may be used to determine a time remaining until some action is required (180). For instance, this may be a time until an ERI or EOL must be activated for a non-rechargeable battery, or a time remaining until a recharge session must be initiated for a rechargeable battery. In some instances, an action may be taken as a result of the time-remaining determination (182). For instance, an ERI or EOL indication may be activated, or a warning may be issued that a recharge session must be initiated.

In accordance with the foregoing, some notification containing status and other data may be provided to a user interface device (184). Such a user interface device may be provided on a patient programmer, a clinician programmer, an external recharge unit, a personal computer, or some other device. This user interface may include a display screen for providing a text message, an icon, and/or some other visual indication. The user interface may alternatively or additionally include a device for generating an audio signal such as a warning tone or a message delivered via electronically-synthesized speech. A tactile feedback device such as one that generates a vibration may also be provided. Any other type of device that may be used to communicate information to a user may be used instead of, or in addition to, those discussed above. The status and/or data communicated in this manner may include the value derived for the battery impedance, the value obtained for the open-circuit voltage, the battery capacity, the time remaining until an action is required, information pertaining to the action that is required, any of the voltage or current values $V_0$-$V_2$ and/or $I_0$-$I_2$, and/or other information that will aid a user in preparing for an action to be taken concerning the battery.

It will be appreciated that the flowchart of FIG. 12 is merely exemplary, and many alternative embodiments are possible within the scope of the invention. As an example, step 148 involving the activation of the second current source may instead involve activating both of the first and second current sources, each of which generates a current of a same predetermined amplitude. In this case, impedance is determined as follows, as was discussed above:

$$Z_{BATTERY}=(V_1-V_2)/(I_1)=(V_1-V_2)/(I_2)$$

One or more of the steps of FIG. 12 may be performed by a control circuit 66 (FIG. 3), which may be a microprocessor that is executing software or firmware instructions stored within one or more of storage devices 68. Alternatively, some or all of the steps may be performed solely in hardware. The results of the steps may then be transmitted during a telemetry uplink session to an external device 46, which may be a clinician or patient programmer, a recharge unit, or some other external device. Alternatively or additionally, some or all of the steps of FIG. 12 may be performed by any combination of hardware, software, and/or firmware residing within one or more external devices, which may be programmers and/or recharge units. Such hardware may include a circuit such as control circuit 47 (FIG. 2), which may include one or more microprocessors, ASICs, DSPs, state machines, discrete components, and/or any other circuitry. Firmware and/or software may reside in storage device(s) 50 of the external device to control execution of control circuit 47. Moreover, in many cases, the various steps of FIG. 12 may be re-ordered without changing the spirit of the invention.

The systems and circuits described herein are also exemplary. For instance, in regards to the systems of FIGS. 2 and 3, many other types of architectures and configurations may be employed for IMD 16, external device 46, and external antenna 48 without departing from the scope of the current invention. Likewise, measuring circuit 84 (FIG. 10) may be replaced by many other circuit designs that are capable of measuring voltage across the battery terminal without disconnecting the battery from the circuit to which it supplies power, and measuring the current being supplied from the battery.

As will be appreciated by one skilled in the art, these and other variations are possible within the scope of the invention. The foregoing examples are illustrative in nature only, and the scope of the invention is to be determined by the claims that follow.

What is claimed is:

1. A system for monitoring a battery of an implantable medical device, comprising:
   a first current source associated with a current having a first predetermined amplitude;
   a second current source associated with a current having a second predetermined amplitude;
   a circuit adapted to be coupled to receive power from the battery, the circuit comprising at least one of a therapy module adapted to deliver therapy to a patient and sensing circuitry adapted to sense a signal from the patient; and
   a control circuit adapted to activate the first current source and obtain a first voltage measurement across the battery while the first current source is activated, to activate the second current source and obtain a second voltage measurement across the battery while the second current source is activated, and to determine impedance of the battery from the first and the second predetermined amplitudes and the first and the second voltage measurements,
   wherein the control circuit is adapted to obtain the first and second voltage measurements across the battery while the circuit that is adapted to be coupled to receive power is coupled to the battery.

2. The system of claim 1, wherein the control circuit is adapted to determine an open-circuit voltage of the battery from the battery impedance.

3. The system of claim 2, further including a storage device adapted to store data indicative of a characteristic of the battery, and wherein the control circuit is adapted to utilize at least one of the battery impedance and the open-circuit battery voltage to reference the data indicative of a characteristic of the battery to thereby determine a time until an action involving the battery is required.

4. The system of claim 1, further including a measurement circuit adapted to measure at least one of a quiescent current being supplied by the battery and a voltage across the battery while the quiescent current is being supplied by the battery, and wherein the control circuit is adapted to determine an open-circuit battery voltage from the battery impedance, the quiescent current, and the voltage across the battery while the quiescent current is being supplied by the battery.

5. The system of claim 1, further including a storage device adapted to store data indicative of characteristics of the battery, and wherein the control circuit is adapted to utilize the battery impedance and the data indicative of characteristics of the battery to determine capacity of the battery.

6. The system of claim 5, wherein the control circuit is adapted to utilized the capacity of the battery to determine at least one of an action that is to be taken regarding the battery and a time remaining until the action is to be taken.

7. The system of claim 6, wherein the action is selected from a group consisting of activating an ERI indicator, activating an EOL indicator, and scheduling a recharge session to recharge the battery.

8. The system of claim 1, further comprising a second control circuit communicatively coupled to the implantable medical device adapted to receive at least one of the first and the second predetermined amplitudes and the first and the second voltage measurements.

9. The system of claim 8, wherein at least one of the control circuit and the second control circuit is adapted to determine at least one of the battery impedance and an open-circuit voltage of the battery.

10. The system of claim 9, wherein the second control circuit is adapted to determine at least one of an action that is to be taken involving the battery and a time until the action is to be taken based on at least one of the battery impedance and the open-circuit voltage of the battery.

11. The system of claim 8, wherein a programmer comprises the second control circuit.

12. The system of claim 8, wherein a recharge unit comprises the second control circuit.

13. The system of claim 1, wherein the control circuit is adapted to determine the impedance of the battery as (the first voltage measurement−the second voltage measurement) / (the second predetermined amplitude−the first predetermined amplitude).

14. The system of claim 1, wherein the control circuit is adapted to activate the first current source when the circuit that is adapted to be coupled to receive power from the battery is in a passive state.

15. The system of claim 14, wherein the control circuit is adapted to activate the second current source when the circuit that is adapted to be coupled to receive power from the battery is in a passive state.

16. A method of monitoring a battery supplying power to an implantable medical device, comprising:
supplying power, via the battery, to a circuit of the implantable medical device, the circuit comprising at least one of a therapy module adapted to deliver therapy to a patient and sensing circuitry adapted to sense a signal from the patient;
activating, via at least one control circuit, a first current source that sources or sinks a current of a first predetermined amplitude while power is supplied, via the battery, to the circuit;
obtaining, via the at least one control circuit, a first voltage measurement across the battery while the first current source is activated and while power is supplied, via the battery, to the circuit;
activating, via the at least one control circuit, a second current source that sources or sinks a current of a second predetermined amplitude while power is supplied, via the battery, to the circuit;
obtaining, via the at least one control circuit, a second voltage measurement across the battery while the second current source is activated and while power is supplied, via the battery, to the circuit; and
determining, via the at least one control circuit, impedance of the battery from the first predetermined amplitude, the second predetermined amplitude, the first voltage measurement, and the second voltage measurement.

17. The method of claim 16, wherein determining impedance of the battery is performed by the at least one control circuit in the implantable medical device.

18. The method of claim 16, wherein determining impedance of the battery is performed by the at least one control circuit in a device external to the implantable medical device.

19. The method of claim 16, wherein the impedance of the battery is determined as (the first voltage measurement−the second voltage measurement) / (the second predetermined amplitude−the first predetermined amplitude).

20. The method of claim 16, further including utilizing data describing characteristics of the battery to determine, based on the battery impedance, at least one of an action to be taken regarding the battery and a time until the action is to be taken.

21. The method of claim 16, and further including providing status to a user via a user interface device, the status being determined, at least in part, based on the battery impedance, the status being indicative of at least one of an action to be taken regarding the battery, a time until the action is to be taken, a capacity associated with the battery, an open-circuit voltage of the battery, or the battery impedance.

22. The method of claim 16, further including determining an open-circuit voltage of the battery from the impedance of the battery.

23. The method of claim 22, further including utilizing data describing characteristics of the battery to determine, based on at least one of the battery impedance and the open-circuit voltage, at least one of an action to be taken regarding the battery, a time until the action is to be taken and a capacity associated with the battery.

24. The method of claim 16, further including:
measuring a quiescent current being provided by the battery while the implantable medical device is in the quiescent state;
measuring a voltage across the battery while the battery is providing the quiescent current; and
determining, an open-circuit voltage of the battery based on the quiescent current, the battery impedance, and the voltage across the battery while the battery is providing the quiescent current.

25. The method of claim 24, further including placing the implantable medical device in the quiescent state.

26. The method of claim 16, wherein activating, via at least one control circuit, a first current source that sources or sinks a current of a first predetermined amplitude comprises activating, via the at least one control circuit, the first current source at a time when the circuit comprising at least one of a therapy module adapted to deliver therapy to a patient and sensing circuitry adapted to sense a signal from the patient is in a passive state.

27. A system for monitoring a battery of an implantable medical device, comprising:
a circuit adapted to be coupled to receive power from the battery, the circuit comprising at least one of a therapy module adapted to deliver therapy to a patient and sensing circuitry adapted to sense a signal from the patient;

a first current source adapted to cause a current of a first predetermined amplitude to be drawn from the battery while the circuit is coupled to receive power from the battery;

a second current source adapted to cause a current of a second predetermined amplitude to be drawn from the battery while the circuit is coupled to receive power from the battery; and a measurement circuit adapted to measure a first voltage across the battery when a first combination of the first and second current sources is activated while the circuit is coupled to receive power from the battery and to measure a second voltage across the battery when a different combination of the first and the second current sources is activated while the circuit is coupled to receive power from the battery, whereby impedance of the battery is determined from the first predetermined amplitude, the second predetermined amplitude, the first voltage, and the second voltage.

28. The system of claim 27, further comprising a control circuit adapted to determine the battery impedance from the first predetermined amplitude, the second predetermined amplitude, the first voltage, and the second voltage.

29. The system of claim 28, further including an external device adapted to be electromagnetically coupled to the implantable medical device, and wherein the external device comprises the control circuit.

30. The system of claim 28, further comprising an implantable medical device that comprises the control circuit.

31. The system of claim 27, further comprising a storage device adapted to store executable instructions to cause selective activation of at least one of the first current source, the second current source, and the measurement circuit.

32. The system of claim 27, wherein the measurement circuit is adapted to measure a quiescent current that is drawn from the battery when the therapy module is not delivering therapy and both the first current source and the second current source are deactivated.

33. The system of claim 28, wherein the measurement circuit is adapted to measure a quiescent current that is drawn from the battery when the therapy module is not delivering therapy and when both the first current source and the second current source are deactivated, and wherein the control circuit is adapted to determine an open-circuit voltage of the battery from the quiescent current and the battery impedance.

34. The system of claim 28, wherein the control circuit is adapted to determine the battery impedance as (the first voltage measurement−the second voltage measurement) / (the second predetermined amplitude−the first predetermined amplitude).

35. The system of claim 27, further comprising a control circuit adapted to determine, based on the battery impedance, at least one of battery capacity, an action to be performed in association with the battery, and a time until the action is to be performed.

36. The system of claim 27, wherein the measurement circuit is adapted to measure the first voltage across the battery while the circuit is in a passive state and to measure the second voltage across the battery while the circuit is in a passive state.

37. A system for monitoring a battery of an implantable medical device, comprising:

means for receiving power from the battery comprising at least one of therapy means for delivering therapy to a patient and sensing means for sensing a signal from the patient;

first current source means for causing a battery to provide a current of a first predetermined amplitude while the means for receiving receives power from the battery;

second current source means for causing a battery to provide a current of a second predetermined amplitude while the means for receiving receives power from the battery;

measurement means for obtaining a first voltage measurement across the battery when a first combination comprising at least one of the first current source means and the second current source means are selectively activated while the means for receiving receives power from the battery, and for obtaining a second voltage measurement across the battery when a second combination comprising at least one of the first current source means and the second current source means that is different from the first combination is selectively activated while the means for receiving receives power from the battery; and control means for determining impedance of the battery based on the first predetermined amplitude, the second predetermined amplitude, the first voltage measurement, and the second voltage measurement.

38. A method of monitoring a battery supplying power to an implantable medical device, comprising:

coupling a battery to a circuit of the implantable medical device, the circuit comprising at least one of a therapy module adapted to deliver therapy to a patient and sensing circuitry adapted to sense a signal from the patient;

generating a first current having a first predetermined amplitude while the battery is coupled to the circuit;

obtaining a first voltage measurement across the battery while the first current is being generated and while the battery is coupled to the circuit;

generating a second current having a second predetermined amplitude while the battery is coupled to the circuit;

obtaining a second voltage measurement across the battery while the second current source is activated and while the battery is coupled to the circuit; and determining, via a control circuit, impedance of the battery from the first predetermined amplitude, the second predetermined amplitude, the first voltage measurement, and the second voltage measurement.

39. The system of claim 37, wherein the measurement means comprises means for obtaining the first voltage measurement across the battery while the means for receiving is in a passive state.

40. The method of claim 38, wherein generating a first current comprises generating a first current while the circuit comprising at least one of a therapy module and sensing circuitry is in a passive state and wherein generating a second current comprises generating a second current while the circuit comprising at least one of a therapy module and sensing circuitry is in a passive state.

* * * * *